United States Patent
Inoue et al.

(10) Patent No.: US 9,196,844 B2
(45) Date of Patent: Nov. 24, 2015

(54) METHOD OF SYNTHESIZING PYRAZINE DERIVATIVE, AND LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Hideko Inoue, Kanagawa (JP); Tomoya Yamaguchi, Kanagawa (JP); Yasushi Kitano, Kanagawa (JP); Hiromi Seo, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 13/905,829

(22) Filed: May 30, 2013

(65) Prior Publication Data

US 2013/0324729 A1  Dec. 5, 2013

(30) Foreign Application Priority Data

Jun. 1, 2012 (JP) .................................. 2012-125869

(51) Int. Cl.
  *C07D 241/42* (2006.01)
  *C07D 409/10* (2006.01)
  *H01L 51/54* (2006.01)
  (Continued)

(52) U.S. Cl.
  CPC .......... *H01L 51/0071* (2013.01); *C07D 241/42* (2013.01); *C07D 409/10* (2013.01); *H01L 51/0072* (2013.01); *H01L 51/0074* (2013.01); *H01L 27/3206* (2013.01); *H01L 51/0085* (2013.01); *H01L 51/5016* (2013.01); *H01L 51/5028* (2013.01); *H01L 51/5265* (2013.01);
  (Continued)

(58) Field of Classification Search
  CPC ............... C07D 241/42; C07D 409/10; H01L 2251/308; H01L 27/3206; H01L 51/0071; H01L 51/0085; H01L 51/5016; H01L 51/5028; H01L 51/5265; H01L 51/5278
  See application file for complete search history.

(56) References Cited

U.S. PATENT DOCUMENTS 4,129,661 A * 12/1978 Roszkowski et al. ......... 514/392
6,723,445 B2    4/2004 Li et al.
(Continued)

FOREIGN PATENT DOCUMENTS

EP       1 962 354 A1      8/2008
JP       2011-201869      10/2011
WO       WO 2008/031743 A1   3/2008

OTHER PUBLICATIONS

Anuradha et al. (Acta Cryst. (2009). E65, o106; sup1-sup8).*
(Continued)

*Primary Examiner* — Valerie Rodriguez-Garcia
(74) *Attorney, Agent, or Firm* — Husch Blackwell LLP

(57) ABSTRACT

A novel method includes a synthetic pathway in which α-diketone and a 1-(haloaryl)ethane-1,2-diamine derivative are cyclized to each other to form a 2-(haloaryl)pyrazine derivative. Further, a 2-arylpyrazine derivative having an aryl group or a heteroaryl group as a substituent is synthesized by coupling the 2-(haloaryl)pyrazine derivative obtained by the above synthetic pathway and an arylboronic acid or a heteroarylboronic acid. The 2-arylpyrazine derivative obtained by the novel method is useful for a light-emitting element, a light-emitting device, an electronic device, or a lighting device with high emission efficiency.

10 Claims, 13 Drawing Sheets

(51) Int. Cl.
  *H01L 51/00* (2006.01)
  *H01L 51/50* (2006.01)
  *H01L 51/52* (2006.01)
  *H01L 27/32* (2006.01)

(52) U.S. Cl.
  CPC ....... *H01L 51/5278* (2013.01); *H01L 2251/308* (2013.01)

(56) References Cited

U.S. PATENT DOCUMENTS

| | | | |
|---|---|---|---|
| 7,355,340 B2 | 4/2008 | Shitagaki et al. | |
| 7,601,435 B2 | 10/2009 | Shitagaki et al. | |
| 7,927,720 B2 | 4/2011 | Nomura et al. | |
| 7,931,974 B2 | 4/2011 | Egawa et al. | |
| 7,993,494 B2 | 8/2011 | Inoue et al. | |
| 8,048,540 B2 * | 11/2011 | Inoue et al. | 428/690 |
| 8,084,146 B2 | 12/2011 | Murase et al. | |
| 8,119,259 B2 | 2/2012 | Kadoma et al. | |
| 8,138,303 B2 | 3/2012 | Chebotareva et al. | |
| 8,178,216 B2 | 5/2012 | Nomura et al. | |
| 8,314,101 B2 | 11/2012 | Kadoma et al. | |
| 2005/0064237 A1 | 3/2005 | Kato et al. | |
| 2009/0026922 A1 | 1/2009 | Iwaki et al. | |
| 2009/0072718 A1 | 3/2009 | Nomura et al. | |
| 2009/0153041 A1 | 6/2009 | Kawakami et al. | |
| 2009/0184633 A1 | 7/2009 | Kadoma et al. | |
| 2010/0039024 A1 | 2/2010 | Wendeborn et al. | |
| 2010/0090588 A1 | 4/2010 | Yokoyama et al. | |
| 2011/0089407 A1 * | 4/2011 | Schmidhalter et al. | 257/40 |
| 2011/0210316 A1 * | 9/2011 | Kadoma et al. | 257/40 |
| 2012/0074390 A1 | 3/2012 | Seo et al. | |
| 2012/0104373 A1 | 5/2012 | Inoue et al. | |
| 2012/0193613 A1 | 8/2012 | Kadoma et al. | |
| 2012/0197020 A1 | 8/2012 | Osaka et al. | |
| 2013/0048971 A1 | 2/2013 | Kitano et al. | |
| 2013/0060033 A1 | 3/2013 | Seo et al. | |
| 2013/0075704 A1 | 3/2013 | Takasu et al. | |
| 2013/0082591 A1 | 4/2013 | Seo et al. | |
| 2013/0112954 A1 | 5/2013 | Osaka et al. | |

OTHER PUBLICATIONS

Slusarczyk et al. (Letters in Drug Design & Discovery, 2009, 6, 478-486).*
Ghosh et al. (Bioorg. Med. Chem. 11 (2003) 629-657).*
Zhang, M. et al., "Highly-Efficient Solution-Processed OLEDs Based on New Bipolar Emitters," Chemical Communications, 2010, vol. 46, pp. 3923-3925.
Wermuth, C.G. "Molecular Variations Based on Isosteric Replacements," *The Practice of Medicinal Chemistry*, 1996, Adademic Press, Ltd. pp. 204-237.

* cited by examiner

METHOD OF SYNTHESIZING PYRAZINE DERIVATIVE, AND LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to a novel method of synthesizing a pyrazine derivative, and to a light-emitting element, a light-emitting device, an electronic device, and a lighting device using a pyrazine derivative obtained by the synthesizing method.

2. Description of the Related Art

A light-emitting element with a structure in which an EL layer is provided between a pair of electrodes is a self-luminous light-emitting element in which carriers (holes or electrons) are injected from the pair of electrodes by application of an electric field, and recombined in the EL layer to generate energy, resulting in light emission.

An organic compound is mainly used as an EL material used for the EL layer in the light-emitting element. Since an organic compound has a significant influence on improvement in element characteristics of the light-emitting element, a variety of novel organic compounds has been developed (e.g., see Patent Document 1).

REFERENCE

Patent Document

[Patent Document 1] Japanese Published Patent Application No. 2011-201869

SUMMARY OF THE INVENTION

A simple and inexpensive method is preferable for synthesizing a novel organic compound. A substance (an impurity) which cannot be technically removed in a course of synthesis is a problem for establishing the synthesizing method. For example, a method of synthesizing a pyrazine derivative via a synthetic pathway of a pyrazine halide derivative, which is a synthetic intermediate, whose pytazine skeleton is halogenated is known (e.g., see Patent Document 1). A halogen body of an EL material may be generated as an impurity derived from this pyrazine halide derivative. This is because a plurality of halogenated impurities is easily contained in a pyrazine skeleton of the pyrazine halide derivative that is a synthetic intermediate. It is difficult to completely remove the halogen body of the EL material by purification or the like, and thus there is a possibility that the halogen body of the EL material is contained in a final product.

Note that formation of the EL layer affects the element characteristics of the light-emitting element and thus is very important for forming the light-emitting element. In the case where the EL material used for the EL layer contains a halogen body of the EL material, there is a problem in that the element characteristics of the light-emitting element are decreased.

In view of the above, one embodiment of the present invention provides a novel method in which a pyrazine derivative is synthesized without a synthetic pathway of a pyrazine halide derivative, which is a synthetic intermediate, whose pytazine skeleton is halogenated. Another embodiment of the present invention provides a light-emitting element, a light-emitting device, an electronic device, or a lighting device with high emission efficiency by using a pyrazine derivative obtained by the above synthesizing method as an EL material.

One embodiment of the present invention is a method of synthesizing a pyrazine derivative without a synthetic pathway of a pyrazine halide derivative, which is a synthetic intermediate, whose pytazine skeleton is halogenated. Specifically, one embodiment of the present invention is a method of synthesizing a 2-arylpyrazine derivative having an aryl group or a heteroaryl group as a substituent.

Note that the above synthesizing method includes a synthetic pathway in which α-diketone and a 1-(haloaryl)ethane-1,2-diamine derivative are condensed and cyclized to each other to form a 2-(haloaryl)pyrazine derivative. Examples of α-diketone include glyoxal, 1-phenyl glyoxal, benzil, and 9,10-phenanthrenequinone in which phenyl groups of benzil are bonded to each other at the ortho position.

Another embodiment of the present invention is a method of synthesizing a 2-arylpyrazine derivative having an aryl group or a heteroaryl group as a substituent, which is synthesized by coupling a 2-(haloaryl)pyrazine derivative obtained by the above synthesizing method and an arylboronic acid or a heteroarylboronic acid.

Another embodiment of the present invention is a light-emitting element including the pyrazine derivative synthesized by the above synthesizing methods (specifically, a 2-arylpyrazine derivative having an aryl group or a heteroaryl group as a substituent, which is obtained by coupling a 2-(haloaryl)pyrazine derivative and an arylboronic acid or a heteroarylboronic acid).

Note that one embodiment of the present invention includes not only a light-emitting device including the light-emitting element but also an electronic device and a lighting device each including the light-emitting device. Accordingly, a light-emitting device in this specification refers to an image display device or a light source (including a lighting device). The light-emitting device also includes the following modules in its category: a module in which a connector such as a flexible printed circuit (FPC) or a tape carrier package (TCP) is attached to a light-emitting device; a module having a TCP at the end of which a printed wiring board is provided; and a module having an integrated circuit (IC) directly mounted over a light-emitting device by a chip on glass (COG) method.

According to one embodiment of the present invention, a method of synthesizing a pyrazine derivative without a synthetic pathway of a pyrazine halide derivative, which is a synthetic intermediate, whose pytazine skeleton is halogenated can be obtained. Moreover, according to one embodiment of the present invention, a light-emitting element, a light-emitting device, an electronic device, or a lighting device with high emission efficiency and high reliability in which the pyrazine derivative obtained by the above synthesizing method is used as an EL material can be obtained.

DETAILED DESCRIPTION OF THE INVENTION

Figure 1:
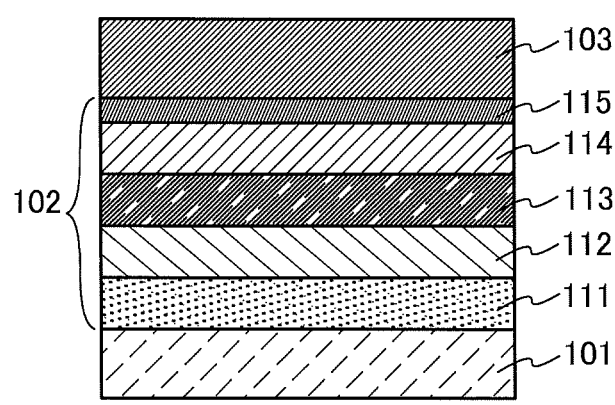
FIG. 1 illustrates a structure of a light-emitting element.

Hereinafter, embodiments of the present invention will be described with reference to the drawings. Note that the present invention is not limited to the following description, and modes and details thereof can be modified in various ways without departing from the spirit and scope of the invention. Therefore, the present invention should not be construed as being limited to the description in the following embodiments.

Embodiment 1

In this embodiment, a method of synthesizing a pyrazine derivative of one embodiment of the present invention will be described.

One embodiment of the present invention is a method of synthesizing a 2-arylpyrazine derivative having an aryl group or a heteroaryl group as a substituent without a synthetic pathway of a pyrazine halide derivative, which is a synthetic intermediate, whose pytazine skeleton is halogenated.

It is necessary for such a synthesizing method, first, to obtain a 2-(haloaryl)pyrazine derivative without a synthetic pathway of a pyrazine halide derivative. The 2-(haloaryl)pyrazine derivative can be obtained by condensing and cyclizing α-diketone and a 1-(haloaryl)ethane-1,2-diamine derivative. This synthesizing method is also one embodiment of the present invention.

For example, a 2-(haloaryl)pyrazine derivative represented by General Formula (G0) can be synthesized by simple Synthesis Scheme (A-1) shown below. That is, as shown in Synthesis Scheme (A-1) below, the 2-(haloaryl)pyrazine derivative represented by General Formula (G0) can be obtained by reaction of 1-(haloaryl)ethane-1,2-diamine (General Formula (A1)) with α-diketone (General Formula (A2)).

Note that in Synthesis Scheme (A-1) below, a represents an aryl group, X represents a halogen element, and n is an integer of 1 or more. Note also that n is preferably any of 1 to 3. Furthermore, $R^1$ and $R^2$ each independently represent hydrogen, an alkyl group, or an aryl group. In the case where $R^1$ and $R^2$ each represent an aryl group, $R^1$ and $R^2$ may be bonded to each other to form a condensed ring. For example, in the case where $R^1$ and $R^2$ each represent a phenyl group, $R^1$ and $R^2$ may be bonded to each other at the ortho position to form a dibenzo[f,h]quinoxaline ring.

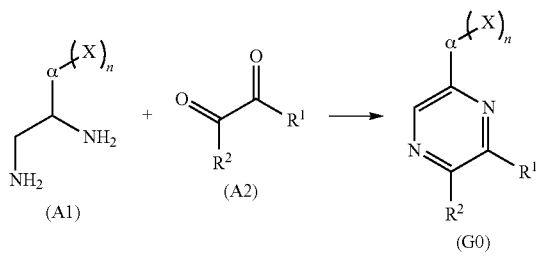

Next, the 2-(haloaryl)pyrazine derivative (General Formula (G0)) obtained by the above synthesizing method is coupled with an arylboronic acid or a heteroarylboronic acid, whereby a 2-arylpyrazine derivative having an aryl group or a heteroaryl group as a substituent can be synthesized. By such a synthesizing method, the 2-arylpyrazine derivative can be synthesized without a synthetic pathway of a pyrazine halide derivative whose pytazine skeleton is halogenated.

For example, a 2-arylpyrazine derivative having an aryl group or a heteroaryl group (Ar) as a substituent, which is represented by General Formula (G1) below, can be synthesized by simple Synthesis Scheme (A-2) shown below.

Specifically, as shown in Synthesis Scheme (A-2) below, the 2-(haloaryl)pyrazine derivative represented by General Formula (G0) (see Synthesis Scheme (A-1)) is coupled with an arylboronic acid or a heteroarylboronic acid represented by General Formula (A3), whereby the 2-arylpyrazine derivative (General Formula (G1)) can be synthesized.

Note that in Synthesis Scheme (A-2) below, α represents an aryl group, X represents a halogen element, and n is an integer of 1 or more. Note also that n is preferably any of 1 to 3. Furthermore, $R^1$ and $R^2$ each independently represent hydrogen, an alkyl group, or an aryl group. In the case where $R^1$ and $R^2$ each represent an aryl group, $R^1$ and $R^2$ may be bonded to each other to form a condensed ring. For example, in the case where $R^1$ and $R^2$ each represent a phenyl group, $R^1$ and $R^2$ may be bonded to each other at the ortho position to form a dibenzo[f,h]quinoxaline ring. Furthermore, Ar represents an aryl group or a heteroaryl group. Note that although a boronic acid is used in General Formula (A3), a dialkoxyboryl group such as a pinacolboryl group may be used instead of a dihydroxyboryl group of the boronic acid.

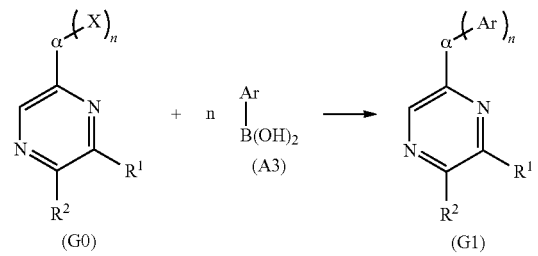

A light-emitting element using the 2-arylpyrazine derivative (specifically, see General Formula (G1)) synthesized by the above synthesizing method can have a longer lifetime than a light-emitting element using the 2-arylpyrazine derivative synthesized via a synthetic pathway of a pyrazine halide derivative whose pytazine skeleton is halogenated, as described in Example below. One of the reasons is provably that the pyrazine halide derivative whose pytazine skeleton is halogenated causes the following problems.

For example, in the case where the 2-arylpyrazine derivative having an aryl group or a heteroaryl group (Ar) as a substituent, which is represented by General Formula (G1), is synthesized via a synthetic pathway of a pyrazine halide derivative, the pyrazine halide derivative (General Formula (B1)) is coupled with an arylboronic acid (General Formula (B2)) having an aryl group or a heteroaryl group (Ar) as a substituent, as shown in Synthesis Scheme (B-2) below. Note that $X^1$ represents a halogen element. The descriptions of the other symbols correspond to those in Synthesis Scheme (A-2).

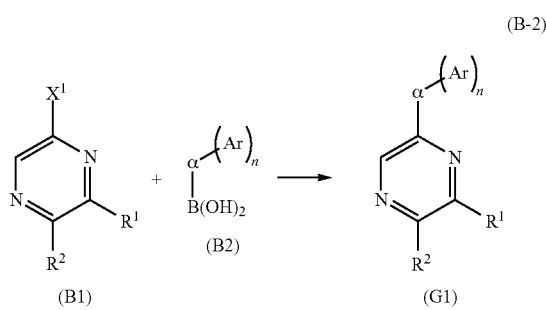

(B-2)

In this case, the pyrazine halide derivative (General Formula (B1)) that is a source material generally contains dihalide or polyhalide represented by the following formula (General Formula (B1')) as an impurity (note that $X^2$ also represents a halogen element as well as $X^1$). Particularly in the case where $X^1$ represents chlorine, the pyrazine halide derivative contains more impurities and thus separation and purification are difficult. When the reaction shown in Synthesis Scheme (B-2) is performed using the pyrazine halide derivative containing such an impurity (General Formula (B1')), $X^2$ is not terminated with a boronic acid (General Formula (B2)); consequently, an impurity (General Formula (G1')) that is a halogen body of a target substance (General Formula (G1)) is generated as shown in Synthesis Scheme (B-2') below. Such an impurity (General Formula (G1')) adversely affects the reliability of the light-emitting element to a great extent.

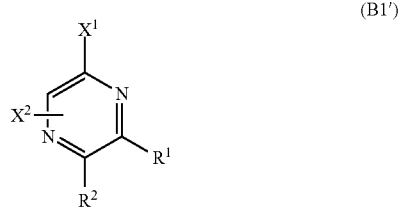

(B1')

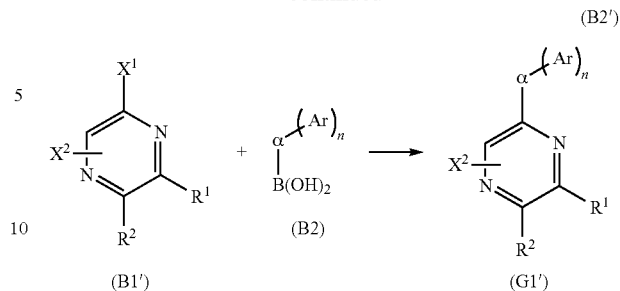

In the above reaction in Synthesis Scheme (B-2'), if the boronic acid (General Formula (B2)) can terminate both $X^1$ and $X^2$, adverse effect due to the impurity (General Formula (G1')) can be avoided. However, particularly in the case of a pyrazine halide derivative in which $X^1$ and $X^2$ are bonded to adjacent carbons (i.e., a pyrazine halide derivative in which $X^1$ and $X^2$ are bonded to the 2-position and the 3-position of the pyrazine), it is difficult to terminate both $X^1$ and $X^2$ with boronic acids (General Formula (B2)) because of the large steric hindrance. That is, it is difficult to suppress the generation of the impurity (General Formula (G1')). Moreover, the property of the impurity (General Formula (G1')) is similar to that of the target substance (General Formula (G1)); therefore, once the impurity is generated, it is difficult to separate the impurity from the target substance. Particularly in the case where $R^1$ and $R^2$ each represent a phenyl group and the phenyl groups are bonded to each other at the ortho position to form a dibenzo[f,h]quinoxaline ring, the solubility is low and the separation is difficult.

For the above reason, at least in terms of suppressing the generation of the impurity (General Formula (G1')), it is effective to obtain the 2-arylpyrazine derivative having an aryl group or a heteroaryl group as a substituent by using the synthesizing methods shown in Synthesis Schemes (A-1) and (A-2).

Since a wide variety of the above-described compounds (General Formula (A1) and General Formula (A2)) is commercially available or its synthesis is feasible, a great variety of 2-(haloaryl)pyrazine derivatives represented by General Formula (G0) can be synthesized. Thus, the pyrazine derivative obtained by the synthesizing method of one embodiment of the present invention has a feature of wide variations.

Note that in one embodiment of the present invention described above, it is preferable that α represent a phenyl group and n be 1 or 2, in which case, 1-(haloaryl)ethane-1,2-diamine represented by General Formula (A1) can be easily obtained. For example, 1-(3-bromophenyl)ethane-1,2-diamine, 1-(4-bromophenyl)ethane-1,2-diamine, or 1-(3,5-dibromophenyl)ethane-1,2-diamine can be easily obtained or synthesized.

The molecular weight of the 2-arylpyrazine derivative having an aryl group or a heteroaryl group as a substituent, which is synthesized by one embodiment of the present invention, is preferably greater than or equal to 400 and less than or equal to 2000. In the case where the molecular weight is less than 400, film quality is reduced because of crystallization or the like at the time of forming a light-emitting element, which adversely affects the reliability of the light-emitting element. In the case where the molecular weight is greater than 2000, it is difficult to perform purification by sublimation or vacuum evaporation.

The method of synthesizing a pyrazine derivative of one embodiment of the present invention is described above.

Since the pyrazine derivative obtained by the synthesizing method of one embodiment of the present invention is synthesized without a synthetic pathway of a pyrazine halide derivative, which is a synthetic intermediate, whose pytazine skeleton is halogenated, a final product can be synthesized without containing halogen. By using the pyrazine derivative synthesized by the synthesizing method of one embodiment of the present invention as an EL material, a light-emitting element, a light-emitting device, an electronic device, or a lighting device with high emission efficiency and high reliability can be achieved. In addition, a light-emitting element, a light-emitting device, an electronic device, or a lighting device with low power consumption can be achieved.

Note that the structure in this embodiment can be combined as appropriate with any structure described in the other embodiments.

Embodiment 2

In this embodiment, referring to FIG. 1, description is made of a light-emitting element in which a pyrazine derivative obtained by the synthesizing method of one embodiment of the present invention is used as an EL material in an EL layer.

In a light-emitting element described in this embodiment, as illustrated in FIG. 1, an EL layer 102 including a light-emitting layer 113 is provided between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, and the like in addition to the light-emitting layer 113.

By application of voltage to such a light-emitting element, holes injected from the first electrode 101 side and electrons injected from the second electrode 103 side recombine in the light-emitting layer 113, and a light-emitting substance emits light based on energy generated at the recombination.

A specific example in which the light-emitting element described in this embodiment is formed is described below.

As the first electrode (anode) 101 and the second electrode (cathode) 103, a metal, an alloy, an electrically conductive compound, a mixture thereof, and the like can be used. Specifically, indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (e.g., MgAg or AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method, an evaporation method (including a vacuum evaporation method), or the like.

The hole-injection layer 111 included in the EL layer 102 contains a substance having a high hole-transport property and an acceptor substance. When electrons are extracted from the substance having a high hole-transport property owing to the acceptor substance, holes are generated. The hole-transport layer 112 is a layer containing a substance having a high hole-transport property and transports holes to the light-emitting layer 113. Thus, holes are injected from the hole-injection layer 111 into the light-emitting layer 113 through the hole-transport layer 112.

As the substance having a high hole-transport property used for the hole-injection layer 111 and the hole-transport layer 112, the following can be given, for example: aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); and the like. Alternatively, the following carbazole derivative can be used: 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-Carbazole (abbreviation: CzPA). The substances mentioned here are mainly ones that have a hole mobility of $10^{-6}$ cm$^2$/V·s or higher. However, a substance other than the above-described substances may also be used as long as the hole-transport property is higher than the electron-transport property.

Furthermore, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), or poly[N,N'-bis (4-butylphenyl)-N,N'-bis(phenyl)benzidine] (abbreviation: Poly-TPD) can be used.

As examples of the acceptor substance that is used for the hole-injection layer 111, a transition metal oxide or an oxide of a metal belonging to any of Group 4 to Group 8 of the periodic table can be given. Specifically, molybdenum oxide is particularly preferable.

The light-emitting layer 113 contains at least a light-emitting substance. Note that the light-emitting layer 113 can be formed by combining a phosphorescent organic metal complex (a guest material) that is a light-emitting substance and a substance having a higher triplet excitation energy than the guest material (a host material). The pyrazine derivative obtained by the synthesizing method of one embodiment of the present invention is suitably used as the host material in the light-emitting layer 113.

Preferable examples of the substance (i.e., host material) used for dispersing the guest material are as follows: compounds having an arylamine skeleton, such as 4-phenyl-4'-(9-phenyl-9H-carbazol-3-yl)triphenylamine (abbreviation: PCBA1BP), 3-[N-(1-naphthyl)-N-(9-phenylcarbazol-3-yl)amino]-9-phenylcarbazole (abbreviation: PCzPCN1), 2,3-bis(4-diphenylaminophenyl)quinoxaline (abbreviation: TPAQn), and NPB; carbazole derivatives such as CBP and 4,4',4''-tris(N-carbazolyl)triphenylamine (abbreviation: TCTA); nitrogen-containing heteroaromatic compounds such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III); and metal complexes such as bis[2-(2-hydroxyphenyl)pyridinato]zinc (abbreviation: Znpp$_2$), bis[2-(2-hydroxyphenyl)benzoxazolato]zinc (abbreviation: Zn(BOX)$_2$), bis(2-methyl-8-quinolinolato)(4-phenylphenolato)aluminum (abbreviation: BAlq), and tris(8-quinolinolato)aluminum (abbreviation: Alq$_3$). Alternatively, a high molecular compound such as PVK can be used.

Note that in the case where the light-emitting layer 113 contains the above-described guest material and host material, phosphorescence with high emission efficiency can be obtained from the light-emitting layer 113.

The electron-transport layer 114 contains a substance having a high electron-transport property. For the electron-transport layer 114, it is possible to use a metal complex such as Alq$_a$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, or bis[2-(2-hydroxyphenyl)benzothiazolato]zinc (abbreviation: Zn(BTZ)$_2$). Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can be used. Further alternatively, a high molecular compound such as poly(2,5-pyridinediyl) (abbreviation: PPy), poly[(9,9-dihexylfluorene-2,7-diyl)-co-(pyridine-3,5-diyl)](abbreviation: PF-Py) or poly[(9,9-dioctylfluorene-2,7-diyl)-co-(2,2'-bipyridine-6,6'-diyl)] (abbreviation: PF-BPy) can be used. The substances mentioned here are mainly ones that have an electron mobility of $10^{-6}$ cm$^2$/V·s or higher. Note that any substance other than the above substances may be used for the electron-transport layer as long as the electron-transport property is higher than the hole-transport property.

Furthermore, the electron-transport layer is not limited to a single layer, and two or more layers made of the aforementioned substances may be stacked.

The electron-injection layer 115 contains a substance having a high electron-injection property. For the electron-injection layer 115, an alkali metal, an alkaline earth metal, magnesium (Mg), or a compound of any of the above metals such as lithium fluoride (LiF), cesium fluoride (CsF), calcium fluoride (CaF$_2$), or lithium oxide (LiO$_x$) can be used. Alternatively, a rare earth metal compound like erbium fluoride (ErF$_3$) can be used. Further alternatively, the above-described substances for forming the electron-transport layer 114 can be used.

Alternatively, a composite material in which an organic compound and an electron donor (donor) are mixed may be used for the electron-injection layer 115. Since electrons are generated in the organic compound by the electron donor, the composite material is superior in an electron-injection property and an electron-transport property. In this case, the organic compound is preferably a material excellent in transporting the generated electrons. Specifically, the above-described substances for forming the electron-transport layer 114 (e.g., a metal complex and a heteroaromatic compound) or the like can be used. As the electron donor, any substance which shows an electron-donating property with respect to the organic compound may be used. Preferable examples are an alkali metal, an alkaline earth metal, and a rare earth metal. Specifically, lithium, cesium, calcium, erbium, ytterbium, and magnesium can be given. Further, an alkali metal oxide and an alkaline earth metal oxide are preferable, and a lithium oxide, a calcium oxide, a barium oxide, and the like can be given. Alternatively, Lewis base such as magnesium oxide can be used. Further alternatively, an organic compound such as tetrathiafulvalene (abbreviation: TTF) can be used.

Note that each of the above-described hole-injection layer 111, hole-transport layer 112, light-emitting layer 113, electron-transport layer 114, and electron-injection layer 115 can be formed by a method such as an evaporation method (e.g., a vacuum evaporation method), an inkjet method, or a coating method.

In the above-described light-emitting element, current flows due to a potential difference generated between the first electrode 101 and the second electrode 103 and holes and electrons recombine in the EL layer 102, so that light based on energy generated at the recombination is emitted. Then, the emitted light is extracted outside through either the first electrode 101 or the second electrode 103 or both. Therefore, either the first electrode 101 or the second electrode 103 or both are electrodes having a light-transmitting property.

Note that the light-emitting element described in this embodiment is an example of a light-emitting element in which the pyrazine derivative obtained by the synthesizing method of one embodiment of the present invention is used as an EL material. As a structure of a light-emitting device including the above light-emitting element, a passive matrix type light-emitting device and an active matrix type light-emitting device can be manufactured. It is also possible to manufacture a light-emitting device with a microcavity structure including a light-emitting element, which is different from the above light-emitting elements, described in another embodiment. Each of the above light-emitting devices is included in the present invention.

Note that there is no particular limitation on a structure of the TFT in the case of manufacturing the active matrix type light-emitting device. For example, a staggered TFT or an inverted staggered TFT can be used as appropriate. Further, a driver circuit formed over a TFT substrate may be formed using either an n-channel TFT or a p-channel TFT or both. Furthermore, there is no particular limitation on the crystallinity of a semiconductor film used for the TFT. For example, an amorphous semiconductor film, a crystalline semiconductor film, an oxide semiconductor film, or the like can be used.

Note that the structure described in this embodiment can be used in combination with any of the structures described in the other embodiments, as appropriate.

Embodiment 3

In this embodiment, description is made of a light-emitting element in which two or more kinds of organic compounds, at least one of which includes a pyrazine derivative obtained by the synthesizing method of one embodiment of the present invention, and a phosphorescent compound are contained in a light-emitting layer.

Figure 2:
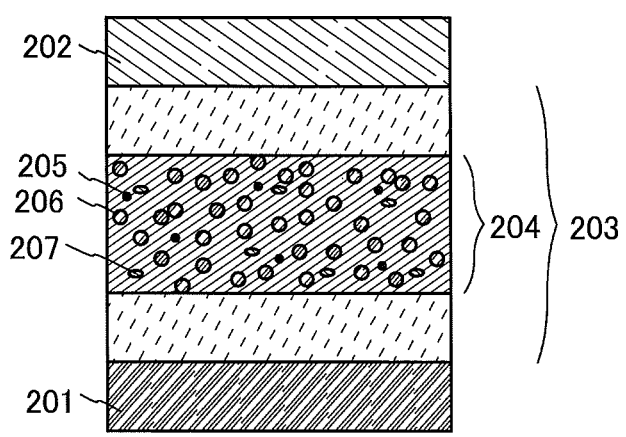
FIG. 2 illustrates a structure of a light-emitting element.

A light-emitting element described in this embodiment includes an EL layer 203 between a pair of electrodes (an anode 201 and a cathode 202) as illustrated in FIG. 2. Note that the EL layer 203 includes at least a light-emitting layer 204 and may include a hole-injection layer, a hole-transport layer, an electron-transport layer, an electron-injection layer, and the like. Note that for the hole-injection layer, the hole-transport layer, the electron-transport layer, and the electron-injection layer, the substances described in Embodiment 2 can be used.

The light-emitting layer 204 described in this embodiment contains a phosphorescent compound 205, a first organic compound 206, and a second organic compound 207. Note that the phosphorescent compound 205 is a guest material in the light-emitting layer 204. Moreover, one of the first organic compound 206 and the second organic compound 207, the content of which is higher than that of the other in the light-emitting layer 204, is a host material in the light-emitting layer 204. Note that the pyrazine derivative obtained by the synthesizing method of one embodiment of the present invention is suitably used as the first organic compound 206 or the second organic compound 207 contained in the light-emitting layer 204.

With the structure of the light-emitting layer 204 in which the guest material is dispersed in the host material, crystallization of the light-emitting layer can be suppressed. Furthermore, it is possible to suppress concentration quenching due to high concentration of the guest material, and thus the light-emitting element can have higher emission efficiency.

Note that it is preferable that a triplet excitation energy level ($T_1$ level) of each of the first organic compound 206 and the second organic compound 207 be higher than that of the phosphorescent compound 205. This is because, when the $T_1$ level of the first organic compound 206 (or the second organic compound 207) is lower than that of the phosphorescent compound 205, the triplet excitation energy of the phosphorescent compound 205, which contributes to light emission, is quenched by the first organic compound 206 (or the second organic compound 207) and accordingly the emission efficiency is decreased.

Here, for improvement in the energy transfer efficiency from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (a fluorescence spectrum in energy transfer from a singlet excited state, and a phosphorescence spectrum in energy transfer from a triplet excited state) largely overlap with an absorption spectrum of a guest material (specifically, a spectrum in an absorption band on the longest wavelength (lowest energy) side). However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, since a phosphorescence spectrum of the host material is located on a longer wavelength (lower energy) side than the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For that reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of a host material.

Thus, in this embodiment, a combination of the first organic compound and the second organic compound preferably forms an exciplex (also referred to as excited complex). In this case, the first organic compound 206 and the second organic compound 207 form an exciplex at the time of recombination of carriers (electrons and holes) in the light-emitting layer 204. Thus, in the light-emitting layer 204, a fluorescence spectrum of the first organic compound 206 and that of the second organic compound 207 are converted into an emission spectrum of the exciplex which is located on a longer wavelength side. Moreover, when the first organic compound and the second organic compound are selected in such that the emission spectrum of the exciplex largely overlaps with the absorption spectrum of the guest material, energy transfer from a singlet excited state can be maximized. Note that also in the case of a triplet excited state, energy transfer from the exciplex, not from the host material, is assumed to occur.

For the phosphorescent compound 205, the phosphorescent organometallic complex can be used, for example. Although there is no particular limitation on the combination of the first organic compound 206 and the second organic compound 207 as long as they can form an exciplex, a combination of a compound which is likely to accept electrons (a compound having an electron-trapping property) and a compound which is likely to accept holes (a compound having a hole-trapping property) is preferably employed.

As a compound which is likely to accept electrons, a π-electron deficient heteroaromatic compound such as a nitrogen-containing heteroaromatic compound is preferable. For example, a quinoxaline derivative and a dibenzoquinoxaline derivative can be given and examples thereof include 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl) phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), and the like.

As a compound which is likely to accept holes, a π-electron rich heteroaromatic compound (e.g., a carbazole derivative or an indole derivative) or an aromatic amine compound is preferable. For example, the following can be given: 4-phenyl-4'-(9-phenyl-9H-carbazol-3-yl)triphenylamine (abbreviation: PCBA1BP), 4,4'-di(1-naphthyl)-4"-(9-phenyl-9H-carbazol-3-yl)triphenylamine (abbreviation: PCBNBB), 3-[N-(1-naphthyl)-N-(9-phenylcarbazol-3-yl)amino]-9-phenylcarbazole (abbreviation: PCzPCN1), 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenyl-carbazol-3-yl)-N,N-diphenylbenzene-1,3-diamine (abbreviation: PCA2B), N-(9,9-dimethyl-2-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino] spiro-9,9'-bifluorene (abbreviation: DPASF), N,N'-bis[4-(carbazol-9-yl)phenyl]-N,N-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N-phenyl-N-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-

N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N-phenylamino]phenyl}-N-phenylamino)biphenyl (abbreviation: DNIPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

As for the above-described first and second organic compounds 206 and 207, the present invention is not limited to the above examples. The combination is determined so that an exciplex can be formed, the emission spectrum of the exciplex overlaps with the absorption spectrum of the phosphorescent compound 205, and the peak of the emission spectrum of the exciplex has a longer wavelength than the peak of the absorption spectrum of the phosphorescent compound 205.

Note that in the case where a compound which is likely to accept electrons and a compound which is likely to accept holes are used for the first organic compound 206 and the second organic compound 207, carrier balance can be controlled by the mixture ratio of the compounds. Specifically, the ratio of the first organic compound to the second organic compound is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound; accordingly, it is possible to achieve high external quantum efficiency of a light-emitting element.

Note that in another structure of the present invention, the light-emitting layer 204 can be formed using a host molecule having a hole-trapping property and a host molecule having an electron-trapping property as the two kinds of organic compounds other than the phosphorescent compound 205 (guest material) so that a phenomenon (guest coupled with complementary hosts: GCCH) occurs in which holes and electrons are introduced to guest molecules existing in the two kinds of host molecules and the guest molecules are brought into an excited state.

At this time, the host molecule having a hole-trapping property and the host molecule having an electron-trapping property can be respectively selected from the above-described compounds which are likely to accept holes and the above-described compounds which are likely to accept electrons.

Note that although the light-emitting element described in this embodiment is one structural example of a light-emitting element, a light-emitting element having another structure which is described in another embodiment can also be used for a light-emitting device according to one embodiment of the present invention. Further, as a light-emitting device including the above light-emitting element, a passive matrix type light-emitting device and an active matrix type light-emitting device can be manufactured. Each of the above light-emitting devices is included in the present invention.

Note that there is no particular limitation on the structure of the TFT in the case of manufacturing the active matrix type light-emitting device. For example, a staggered TFT or an inverted staggered TFT can be used as appropriate. Further, a driver circuit formed over a TFT substrate may be formed using either an n-channel TFT or a p-channel T or both. Furthermore, there is no particular limitation on the crystallinity of a semiconductor film used for the TFT. For example, an amorphous semiconductor film, a crystalline semiconductor film, an oxide semiconductor film, or the like can be used.

Note that the structure described in this embodiment can be used in combination with any of the structures described in the other embodiments, as appropriate.

Embodiment 4

In this embodiment, description is made of a case of forming a light-emitting element (hereinafter referred to as tandem light-emitting element) with a structure in which a pyrazine derivative obtained by the synthesizing method of one embodiment of the present invention is used as an EL material in an EL layer and a plurality of EL layers is formed with a charge-generation layer interposed therebetween.

Figure 3A:
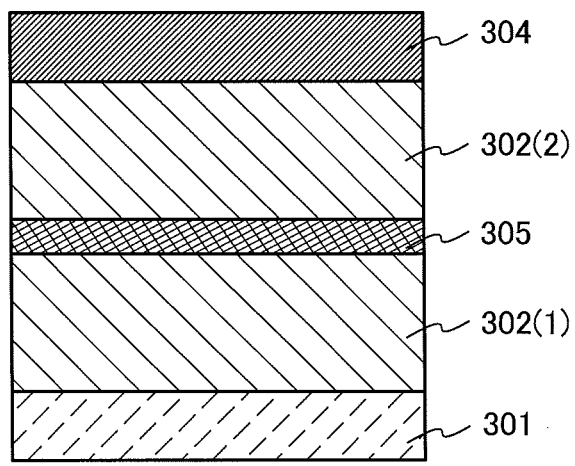
FIGS. 3A and 3B illustrate structures of light-emitting elements.

A light-emitting element described in this embodiment is a tandem light-emitting element including a plurality of EL layers (a first EL layer 302(1) and a second EL layer 302(2)) between a pair of electrodes (a first electrode 301 and a second electrode 304) as illustrated in FIG. 3A.

In this embodiment, the first electrode 301 functions as an anode, and the second electrode 304 functions as a cathode. Note that the first electrode 301 and the second electrode 304 can have structures similar to those described in Embodiment 1. In addition, although the plurality of EL layers (the first EL layer 302(1) and the second EL layer 302(2)) may have structures similar to those described in Embodiment 2 or 3, any of the EL layers may have a structure similar to that described in Embodiment 2 or 3. In other words, the structures of the first EL layer 302(1) and the second EL layer 302(2) may be the same or different from each other and can be similar to those described in Embodiment 2 or 3.

Further, a charge-generation layer 305 is provided between the plurality of EL layers (the first EL layer 302(1) and the second EL layer 302(2)). The charge-generation layer 305 has a function of injecting electrons into one of the EL layers and injecting holes into the other of the EL layers when voltage is applied between the first electrode 301 and the second electrode 304. In this embodiment, when voltage is applied such that the potential of the first electrode 301 is higher than that of the second electrode 304, the charge-generation layer 305 injects electrons into the first EL layer 302(1) and injects holes into the second EL layer 302(2).

Note that in tennis of light extraction efficiency, the charge-generation layer 305 preferably has a light-transmitting property with respect to visible light (specifically, the charge-generation layer 305 has a visible light transmittance of 40% or more). Further, the charge-generation layer 305 functions even if it has lower conductivity than the first electrode 301 or the second electrode 304.

The charge-generation layer 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB) can be used. The substances mentioned here are mainly ones that have a hole mobility of $10^{-6}$ cm$^2$/V·s or higher. However, substances other than the above substances may be used as long as they are organic compounds in which a hole-transport property is higher than an electron-transport property.

Further, as the electron acceptor, 7,7,8,8-tetracyano-2,3,5,6-tetrafluoroquinodimethane (abbreviation: F$_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because their electron-accepting property is high. Among these, molybdenum oxide is especially preferable because it is stable in the air, its hygroscopic property is low, and it is easily treated.

On the other hand, in the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq can be used. Alternatively, a metal complex having an oxazole-based ligand or a thiazole-based ligand, such as Zn(BOX)$_2$ or Zn(BTZ)$_2$ can be used. Further alternatively, other than such a metal complex, PBD, OXD-7, TAZ, BPhen, BCP, or the like can be used. The substances mentioned here are mainly ones that have an electron mobility of 10$^{-6}$ cm$^2$/V·s or higher. Note that any substance other than the above substances may be used as long as the electron-transport property is higher than the hole-transport property.

Further, as the electron donor, an alkali metal, an alkaline earth metal, a rare earth metal, a metal belonging to Group 2 or Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that forming the charge-generation layer 305 by using any of the above materials can suppress an increase in drive voltage caused by the stack of the EL layers.

Figure 3B:
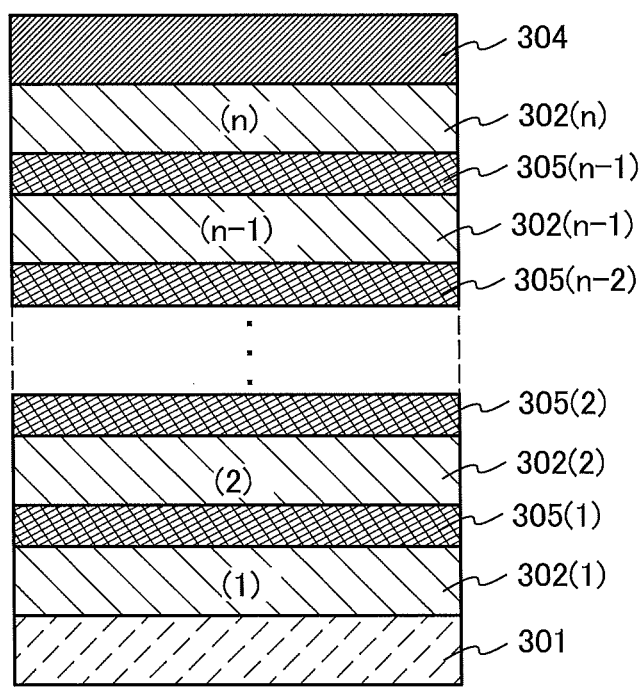

Although this embodiment shows the light-emitting element having two EL layers, the present invention can be similarly applied to a light-emitting element in which n EL layers (n is three or more) are stacked as illustrated in FIG. 3B. In the case where a plurality of EL layers are included between a pair of electrodes as in the light-emitting element according to this embodiment, by provision of a charge-generation layer between the EL layers, light emission in a high luminance region can be obtained with current density kept low. Since the current density can be kept low, the element can have a long lifetime. When the light-emitting element is used for lighting, voltage drop due to resistance of an electrode material can be reduced, thereby achieving homogeneous light emission in a large area. Moreover, a light-emitting device of low power consumption, which can be driven at a low voltage, can be achieved.

Further, by forming EL layers to emit light of different colors from each other, a light-emitting element as a whole can provide light emission of a desired color. For example, by forming a light-emitting element having two EL layers such that the emission color of the first EL layer and the emission color of the second EL layer are complementary colors, the light-emitting element can provide white light emission as a whole. Note that the word "complementary" means color relationship in which an achromatic color is obtained when colors are mixed. That is, white light emission can be obtained by mixture of light from substances, of which the light emission colors are complementary colors.

Further, the same can be applied to a light-emitting element having three EL layers. For example, the light-emitting element as a whole can provide white light emission when the emission color of a first EL layer is red, the emission color of a second EL layer is green, and the emission color of a third EL layer is blue.

Note that the structure described in this embodiment can be used in combination with any of the structures described in the other embodiments, as appropriate.

Embodiment 5

Figure 4:
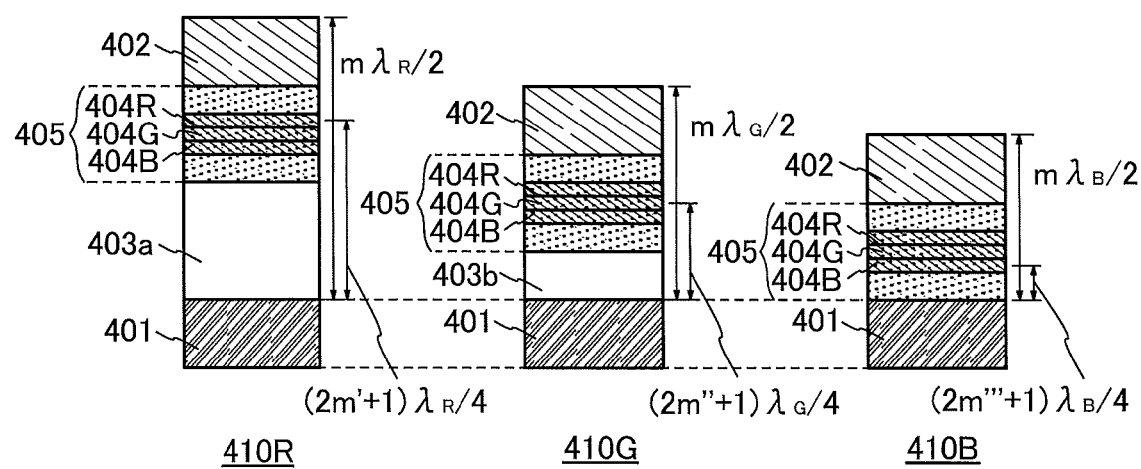
FIG. 4 illustrates a light-emitting device.

A light-emitting device described in this embodiment has a micro optical resonator (microcavity) structure in which a light resonant effect between a pair of electrodes is utilized. The light-emitting device includes a plurality of light-emitting elements each of which has at least an EL layer 405 between a pair of electrodes (a reflective electrode 401 and a semi-transmissive and semi-reflective electrode 402) as illustrated in FIG. 4. Further, the EL layer 405 includes at least a light-emitting layer 404 serving as a light-emitting region and may further include a hole-injection layer, a hole-transport layer, an electron-transport layer, an electron-injection layer, a charge-generation layer, and the like. Note that a pyrazine derivative obtained by the synthesizing method of one embodiment of the present invention can be used as an EL material in the EL layer 405.

In this embodiment, a light-emitting device is described which includes light-emitting elements (a first light-emitting element (R) 410R, a second light-emitting element (G) 410E and a third light-emitting element (B) 410B) having different structures as illustrated in FIG. 4.

The first light-emitting element (R) 410R has a structure in which a first transparent conductive layer 403$a$; an EL layer 405 including a first light-emitting layer (B) 404B, a second light-emitting layer (G) 404E and a third light-emitting layer (R) 404R; and the semi-transmissive and semi-reflective electrode 402 are sequentially stacked over the reflective electrode 401. The second light-emitting element (G) 410G has a structure in which a second transparent conductive layer 403$b$, the EL layer 405, and the semi-transmissive and semi-reflective electrode 402 are sequentially stacked over the reflective electrode 401. The third light-emitting element (B) 410B has a structure in which the EL layer 405 and the semi-transmissive and semi-reflective electrode 402 are sequentially stacked over the reflective electrode 401.

Note that the reflective electrode 401, the EL layer 405, and the semi-transmissive and semi-reflective electrode 402 are common to the light-emitting elements (the first light-emitting element (R) 410R, the second light-emitting element (G) 410G, and the third light-emitting element (B) 410B). The first light-emitting layer (B) 404B emits light (4) having a peak in a wavelength range from 420 nm to 480 nm. The second light-emitting layer (G) 404G emits light ($\lambda_G$) having a peak in a wavelength range from 500 nm to 550 nm. The third light-emitting layer (R) 404R emits light (4) having a peak in a wavelength range from 600 nm to 760 nm. Thus, in each of the light-emitting elements (the first light-emitting element (R) 410R, the second light-emitting element (G) 410E and the third light-emitting element (B) 410B), light emitted from the first light-emitting layer (B) 404B, light emitted from the second light-emitting layer (G) 404G, and light emitted from the third light-emitting layer (R) 404R overlap with each other; accordingly, light having a broad emission spectrum that covers a visible light range can be emitted. Note that the above wavelengths satisfy the relation of $\lambda_B < \lambda_G < \lambda_R$.

Each of the light-emitting elements described in this embodiment has a structure in which the EL layer 405 is interposed between the reflective electrode 401 and the semi-transmissive and semi-reflective electrode 402. Light emitted in all directions from the light-emitting layers included in the EL layer 405 is resonated by the reflective electrode 401 and the semi-transmissive and semi-reflective electrode 402 which function as a micro optical resonator (microcavity). Note that the reflective electrode 401 is formed using a conductive material having reflectivity, and a film whose visible light reflectivity is 40% to 100%, preferably 70% to 100%, and whose resistivity is $1 \times 10^{-2}$ Ω·cm or lower is used. In addition, the semi-transmissive and semi-reflective electrode 402 is formed using a conductive material having reflectivity and a conductive material having a light-transmitting property, and a film whose visible light reflectivity is 20% to 80%, preferably 40% to 70%, and whose resistivity is $1 \times 10^{-2}$ Ω·cm or lower is used.

In this embodiment, the thicknesses of the transparent conductive layers (the first transparent conductive layer 403a and the second transparent conductive layer 403b) provided in the first light-emitting element (R) 410R and the second light-emitting element (G) 410G, respectively, are varied between the light-emitting elements, whereby the light-emitting elements differ in the optical path length from the reflective electrode 401 to the semi-transmissive and semi-reflective electrode 402. In other words, in light having a broad emission spectrum, which is emitted from the light-emitting layers of each of the light-emitting elements, light with a wavelength that is resonated between the reflective electrode 401 and the semi-transmissive and semi-reflective electrode 402 can be enhanced while light with a wavelength that is not resonated therebetween can be attenuated. Thus, when the elements differ in the optical path length from the reflective electrode 401 to the semi-transmissive and semi-reflective electrode 402, light with different wavelengths can be extracted.

Note that the total thickness from the reflective electrode 401 to the semi-transmissive and semi-reflective electrode 402 is set to $m\lambda_R/2$ (m is a natural number) in the first light-emitting element (R) 410R; the total thickness from the reflective electrode 401 to the semi-transmissive and semi-reflective electrode 402 is set to $m\lambda_G/2$ (m is a natural number) in the second light-emitting element (G) 410G; and the total thickness from the reflective electrode 401 to the semi-transmissive and semi-reflective electrode 402 is set to $m\lambda_B/2$ (m is a natural number) in the third light-emitting element (B) 410B.

In this manner, the light ($\lambda_R$) emitted from the third light-emitting layer (R) 404R included in the EL layer 405 is mainly extracted from the first light-emitting element (R) 410R, the light ($\lambda_G$) emitted from the second light-emitting layer (G) 404G included in the EL layer 405 is mainly extracted from the second light-emitting element (G) 410G, and the light ($\lambda_B$) emitted from the first light-emitting layer (B) 404B included in the EL layer 405 is mainly extracted from the third light-emitting element (B) 410B. Note that the light extracted from each of the light-emitting elements is emitted from the semi-transmissive and semi-reflective electrode 402 side.

Further, strictly speaking, the total thickness from the reflective electrode 401 to the semi-transmissive and semi-reflective electrode 402 can be the total thickness from a reflection region in the reflective electrode 401 to a reflection region in the semi-transmissive and semi-reflective electrode 402. However, it is difficult to precisely determine the positions of the reflection regions in the reflective electrode 401 and the semi-transmissive and semi-reflective electrode 402; therefore, it is assumed that the above effect can be sufficiently obtained wherever the reflection regions may be set in the reflective electrode 401 and the semi-transmissive and semi-reflective electrode 402.

Next, in the first light-emitting element (R) 410R, the optical path length from the reflective electrode 401 to the third light-emitting layer (R) 404R is adjusted to a desired thickness ($(2m'+1)\lambda_R/4$, where m' is a natural number); thus, light emitted from the third light-emitting layer (R) 404R can be amplified. Light (first reflected light) that is reflected by the reflective electrode 401 of the light emitted from the third light-emitting layer (R) 404R interferes with light (first incident light) that directly enters the semi-transmissive and semi-reflective electrode 402 from the third light-emitting layer (R) 404R. Therefore, by adjusting the optical path length from the reflective electrode 401 to the third light-emitting layer (R) 404R to the desired value ($(2m'+1)\lambda_R/4$, where m' is a natural number), the phases of the first reflected light and the first incident light can be aligned with each other and the light emitted from the third light-emitting layer (R) 404R can be amplified.

Note that, strictly speaking, the optical path length from the reflective electrode 401 to the third light-emitting layer (R) 404R can be the optical path length from a reflection region in the reflective electrode 401 to a light-emitting region in the third light-emitting layer (R) 404R. However, it is difficult to precisely determine the positions of the reflection region in the reflective electrode 401 and the light-emitting region in the third light-emitting layer (R) 404R; therefore, it is assumed that the above effect can be sufficiently obtained wherever the reflection region and the light-emitting region may be set in the reflective electrode 401 and the third light-emitting layer (R) 404R, respectively.

Next, in the second light-emitting element (G) 410G, the optical path length from the reflective electrode 401 to the second light-emitting layer (G) 404G is adjusted to a desired thickness ($(2m''+1)\lambda_G/4$, where m'' is a natural number); thus, light emitted from the second light-emitting layer (G) 404G can be amplified. Light (second reflected light) that is reflected by the reflective electrode 401 of the light emitted from the second light-emitting layer (G) 404G interferes with light (second incident light) that directly enters the semi-transmissive and semi-reflective electrode 402 from the second light-emitting layer (G) 404G. Therefore, by adjusting the optical path length from the reflective electrode 401 to the second light-emitting layer (G) 404G to the desired value ($(2m''+1)\lambda_G/4$, where m'' is a natural number), the phases of the second reflected light and the second incident light can be aligned with each other and the light emitted from the second light-emitting layer (G) 404G can be amplified.

Note that, strictly speaking, the optical path length from the reflective electrode 401 to the second light-emitting layer (G) 404G can be the optical path length from a reflection region in the reflective electrode 401 to a light-emitting region in the second light-emitting layer (G) 404G. However, it is difficult to precisely determine the positions of the reflection region in the reflective electrode 401 and the light-emitting region in the second light-emitting layer (G) 404G; therefore, it is assumed that the above effect can be sufficiently obtained wherever the reflection region and the light-emitting region may be set in the reflective electrode 401 and the second light-emitting layer (G) 404G respectively.

Next, in the third light-emitting element (B) 410B, the optical path length from the reflective electrode 401 to the first light-emitting layer (B) 404B is adjusted to a desired thickness ($(2m'''+1)\lambda_B/4$, where m''' is a natural number); thus, light emitted from the first light-emitting layer (B) 404B can be amplified. Light (third reflected light) that is reflected by the reflective electrode 401 of the light emitted from the first light-emitting layer (B) 404B interferes with light (third incident light) that directly enters the semi-transmissive and semi-reflective electrode 402 from the first light-emitting layer (B) 404B. Therefore, by adjusting the optical path length from the reflective electrode 401 to the first light-emitting layer (B) 404B to the desired value $((2m'''+1)\lambda_B/4$, where m''' is a natural number), the phases of the third reflected light and the third incident light can be aligned with each other and the light emitted from the first light-emitting layer (B) 404B can be amplified.

Note that, strictly speaking, the optical path length from the reflective electrode 401 to the first light-emitting layer (B) 404B in the third light-emitting element can be the optical path length from a reflection region in the reflective electrode 401 to a light-emitting region in the first light-emitting layer (B) 404B. However, it is difficult to precisely determine the positions of the reflection region in the reflective electrode 401 and the light-emitting region in the first light-emitting layer (B) 404B; therefore, it is assumed that the above effect can be sufficiently obtained wherever the reflection region and the light-emitting region may be set in the reflective electrode 401 and the first light-emitting layer (B) 404B, respectively.

Note that although each of the light-emitting elements in the above-described structure includes a plurality of light-emitting layers in the EL layer, the present invention is not limited thereto; for example, the structure of the tandem light-emitting element which is described in Embodiment 4 can be combined, in which case a plurality of EL layers are provided so that a charge-generation layer is sandwiched therebetween in one light-emitting element and one or more light-emitting layers are formed in each of the EL layers.

The light-emitting device described in this embodiment has a microcavity structure, in which light with wavelengths which differ depending on the light-emitting elements can be extracted even when they include the same EL layers, so that it is not needed to form light-emitting elements for the colors of R, G, and B. Therefore, the above structure is advantageous for full color display owing to easiness in achieving higher resolution display or the like. In addition, emission intensity with a predetermined wavelength in the front direction can be increased, whereby power consumption can be reduced. The above structure is particularly useful in the case of being used for a color display (image display device) including pixels of three or more colors but may also be used for lighting or the like.

Embodiment 6

In this embodiment, description is made of a light-emitting device including a light-emitting element in which a pyrazine derivative obtained by the synthesizing method of one embodiment of the present invention is used as an EL material in a light-emitting layer.

The light-emitting device may be either a passive matrix type light-emitting device or an active matrix type light-emitting device. Note that any of the light-emitting elements described in the other embodiments can be used for the light-emitting device described in this embodiment.

In this embodiment, an active matrix type light-emitting device is described with reference to FIGS. 5A and 5B.

Figure 5A:
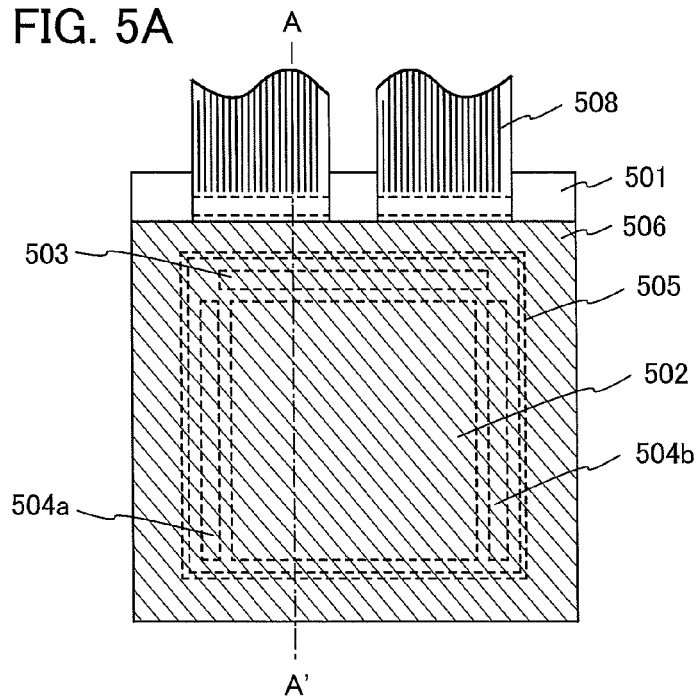
FIGS. 5A and 5B illustrate a light-emitting device.
Figure 5B:
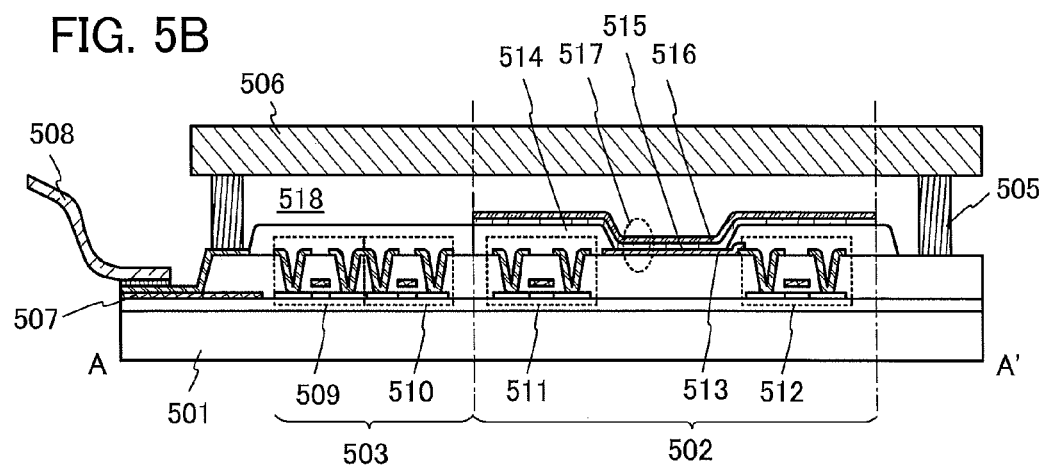

Note that FIG. 5A is a top view illustrating a light-emitting device and FIG. 5B is a cross-sectional view taken along chain line A-A' in FIG. 5A. The active matrix type light-emitting device according to this embodiment includes a pixel portion 502 provided over an element substrate 501, a driver circuit portion (a source line driver circuit) 503, and a driver circuit portion (a gate line driver circuit) 504 (504a and 504b). The pixel portion 502, the driver circuit portion 503, and the driver circuit portion 504 are sealed with a sealant 505 between the element substrate 501 and a sealing substrate 506.

In addition, over the element substrate 501, a lead wiring 507 for connecting an external input terminal, through which a signal (e.g., a video signal, a clock signal, a start signal, a reset signal, or the like) or electric potential from the outside is transmitted to the driver circuit portion 503 and the driver circuit portion 504 (504a and 504b), is provided. Here, an example is described in which a flexible printed circuit (FPC) 508 is provided as the external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure is explained with reference to FIG. 5B. The driver circuit portion and the pixel portion are formed over the element substrate 501; here are illustrated the driver circuit portion 503 which is the source line driver circuit and the pixel portion 502.

An example is illustrated in which a CMOS circuit which is a combination of an n-channel TFT 509 and a p-channel TFT 510 is formed as the driver circuit portion 503. Note that a circuit included in the driver circuit portion may be formed using various CMOS circuits, PMOS circuits, or NMOS circuits. Although a driver integrated type in which the driver circuit is formed over the substrate is described in this embodiment, the driver circuit is not necessarily formed over the substrate, and the driver circuit can be formed outside the substrate.

The pixel portion 502 is formed of a plurality of pixels each of which includes a switching TFT 511, a current control TFT 512, and a first electrode (anode) 513 which is electrically connected to a wiring (a source electrode or a drain electrode) of the current control TFT 512. Note that an insulator 514 is formed to cover end portions of the first electrode (anode) 513. In this embodiment, the insulator 514 is formed using a positive photosensitive acrylic resin.

In addition, in order to obtain favorable coverage by a film which is to be stacked over the insulator 514, the insulator 514 is preferably formed so as to have a curved surface with curvature at an upper edge portion or a lower edge portion. For example, in the case of using a positive photosensitive acrylic resin as a material for the insulator 514, the insulator 514 is preferably formed so as to have a curved surface with a curvature radius (0.2 µm to 3 µm) at the upper edge portion. The insulator 514 can be formed using either a negative photosensitive resin or a positive photosensitive resin. It is possible to use, without limitation to an organic compound, either an organic compound or an inorganic compound such as silicon oxide or silicon oxynitride.

An EL layer 515 and a second electrode (cathode) 516 are stacked over the first electrode (anode) 513. In the EL layer 515, at least a light-emitting layer is provided which contains a pyrazine derivative obtained by the synthesizing method of one embodiment of the present invention. Further, in the EL layer 515, a hole-injection layer, a hole-transport layer, an electron-transport layer, an electron-injection layer, a charge-generation layer, and the like can be provided as appropriate in addition to the light-emitting layer.

Note that a light-emitting element 517 is formed of a stacked structure of the first electrode (anode) 513, the EL layer 515, and the second electrode (cathode) 516. For the first electrode (anode) 513, the EL layer 515, and the second electrode (cathode) 516, the materials described in Embodiment 2 can be used. Although not illustrated, the second electrode (cathode) 516 is electrically connected to an FPC 508 which is an external input terminal.

In addition, although the cross-sectional view of FIG. 5B illustrates only one light-emitting element 517, a plurality of light-emitting elements are arranged in matrix in the pixel portion 502. Light-emitting elements that emit light of three kinds of colors (R, and B) are selectively formed in the pixel portion 502, so that a light-emitting device capable of full color display can be obtained. Alternatively, a light-emitting device which is capable of full color display may be manufactured by a combination with color filters.

Further, the sealing substrate 506 is attached to the element substrate 501 with the sealant 505, so that a light-emitting element 517 is provided in a space 518 surrounded by the element substrate 501, the sealing substrate 506, and the sealant 505. Note that the space 518 may be filled with an inert gas (such as nitrogen and argon) or the sealant 505.

An epoxy-based resin is preferably used for the sealant 505. A material used for these is desirably a material which does not transmit moisture or oxygen as much as possible. As the sealing substrate 506, a plastic substrate formed of fiberglass-reinforced plastics (FRP), polyvinyl fluoride (PVF), polyester, acrylic, or the like can be used besides a glass substrate or a quartz substrate.

As described above, the active matrix type light-emitting device can be obtained.

Note that the structure described in this embodiment can be used in combination with any of the structures described in the other embodiments, as appropriate.

Embodiment 7

In this embodiment, referring to FIGS. 6A to 6D and FIGS. 7A to 7C, descriptions are made of examples of electronic devices manufactured by using the light-emitting device in which a pyrazine derivative obtained by the synthesizing method of one embodiment of the present invention is used as an EL material.

Examples of the electronic devices in which the light-emitting device is used are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices are shown in FIGS. 6A to 6D.

Figure 6A:
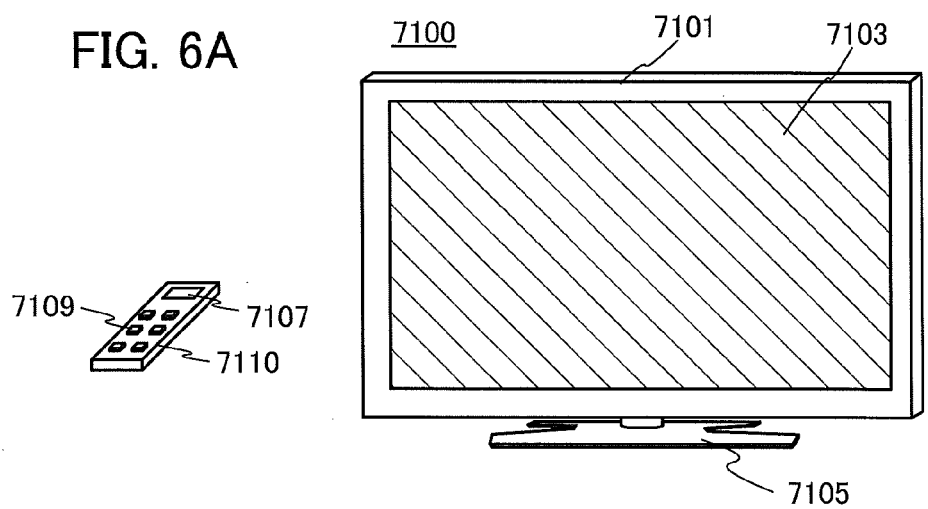
FIGS. 6A to 6D illustrate electronic devices.

FIG. 6A illustrates an example of a television device. In a television device 7100, a display portion 7103 is incorporated in a housing 7101. Images can be displayed by the display portion 7103, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, a general television broadcast can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 6B:
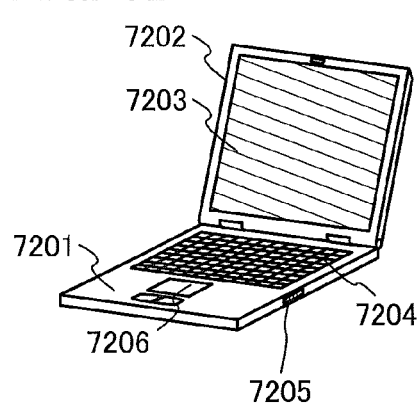

FIG. 6B illustrates a computer, which includes a main body 7201, a housing 7202, a display portion 7203, a keyboard 7204, an external connection port 7205, a pointing device 7206, and the like. This computer is manufactured by using a light-emitting device for the display portion 7203.

Figure 6C:
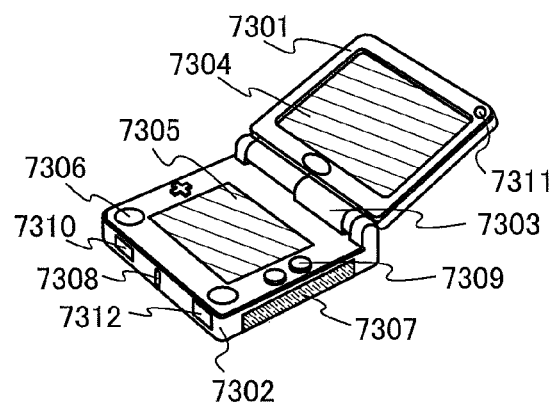

FIG. 6C illustrates a portable game machine having two housings, a housing 7301 and a housing 7302, which are connected with a joint portion 7303 so that the portable game machine can be opened or folded. A display portion 7304 is incorporated in the housing 7301 and a display portion 7305 is incorporated in the housing 7302. In addition, the portable game machine illustrated in FIG. 6C includes a speaker portion 7306, a recording medium insertion portion 7307, an LED lamp 7308, an input unit (an operation key 7309, a connection terminal 7310, a sensor 7311 (sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable game machine is not limited to the above as long as a light-emitting device is used for at least either the display portion 7304 or the display portion 7305, or both, and may include other accessories as appropriate. The portable game machine illustrated in FIG. 6C has a function of reading a program or data stored in a recording medium to display it in the display portion, and a function of sharing information with another portable game machine by wireless communication. Note that the functions of the portable game machine illustrated in FIG. 6C are not limited to these functions, and the portable amusement machine can have various functions.

Figure 6D:
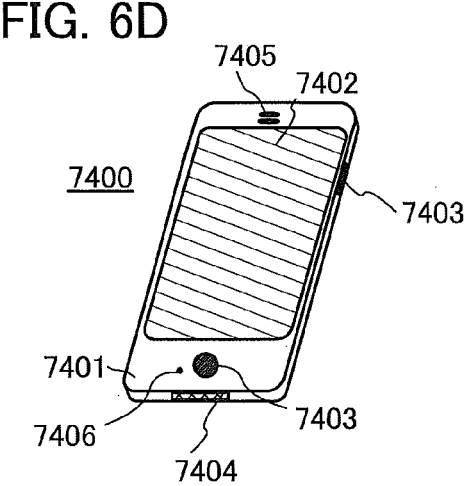

FIG. 6D illustrates an example of a cellular phone. A cellular phone 7400 is provided with a display portion 7402 incorporated in a housing 7401, operation buttons 7403, an external connection port 7404, a speaker 7405, a microphone 7406, and the like. Note that the cellular phone 7400 is manufactured using a light-emitting device for the display portion 7402.

When the display portion 7402 of the cellular phone 7400 illustrated in FIG. 6D is touched with a finger or the like, data can be input into the cellular phone 7400. Further, operations such as making a call and creating e-mail can be performed by touch on the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or creating e-mail, a text input mode mainly for inputting text is selected for the display portion 7402 so that text displayed on a screen can be inputted. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touching the display portion 7402 or operating the operation buttons 7403 of the housing 7401. Alternatively, the screen modes can be switched depending on kinds of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal detected by an optical sensor in the display portion 7402 is detected, the screen mode may be controlled so as to be switched from the input mode to the display mode.

The display portion 7402 may also function as an image sensor. For example, an image of a palm print, a fingerprint, or the like is taken by touch on the display portion 7402 with the palm or the finger, whereby personal authentication can be performed. Further, by providing a backlight or a sensing light source which emits a near-infrared light in the display portion, an image of a finger vein, a palm vein, or the like can be taken.

Figure 7A:
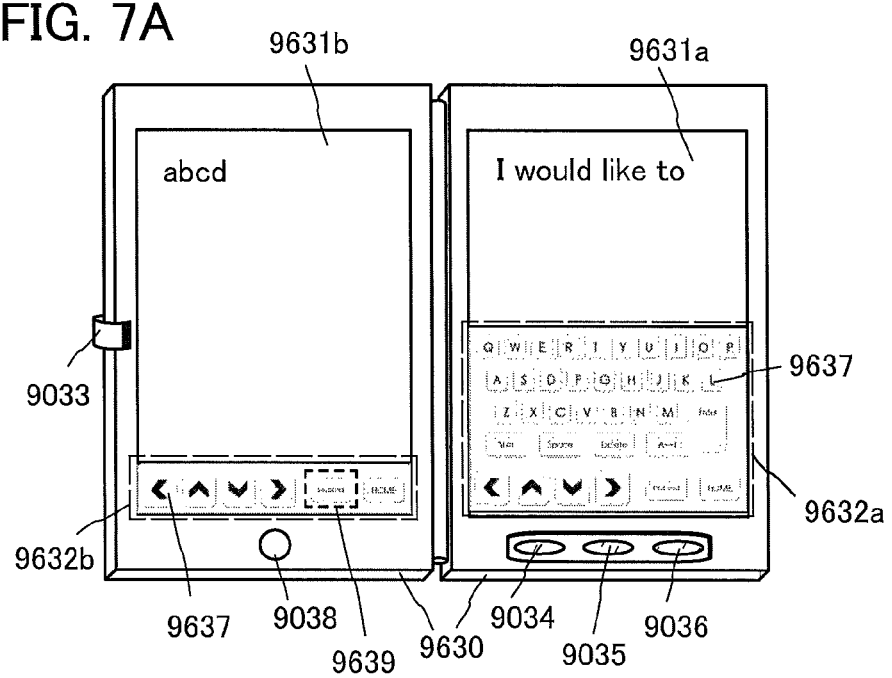
FIGS. 7A to 7C illustrate an electronic device.
Figure 7B:
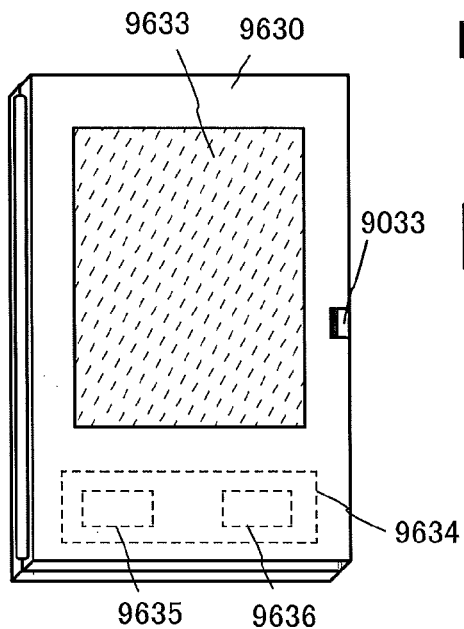

FIGS. 7A and 7B illustrate a tablet terminal that can be folded. In FIG. 7A, the tablet terminal is opened, and includes a housing 9630, a display portion 9631*a*, a display portion 9631*b*, a display-mode switching button 9034, a power button 9035, a power-saving-mode switching button 9036, a clip 9033, and an operation button 9038. The tablet terminal is manufactured using the light-emitting device for one or both of the display portion 9631*a* and the display portion 9631*b*.

A touch panel area 9632*a* can be provided in a part of the display portion 9631*a*, in which area, data can be input by touching displayed operation keys 9637. Note that FIG. 7A shows, as an example, that half of the area of the display portion 9631*a* has only a display function and the other half of the area has a touch panel function. However, the structure of the display portion 9631*a* is not limited to this, and all the area of the display portion 9631*a* may have a touch panel function. For example, all the area of the display portion 9631*a* can display keyboard buttons and serve as a touch panel while the display portion 9631*b* can be used as a display screen.

Like the display portion 9631*a*, part of the display portion 9631*b* can be a touch panel area 9632*b*. When a finger, a stylus, or the like touches the place where a keyboard-display switching button 9639 is displayed in the touch panel, keyboard buttons can be displayed on the display portion 9631*b*.

Touch input can be performed concurrently on the touch panel areas 9632*a* and 9632*b*.

The display-mode switching button 9034 can switch display orientation (e.g., between landscape mode and portrait mode) and select a display mode (switch between monochrome display and color display), for example. With the power-saving-mode switching button 9036, the luminance of display can be optimized in accordance with the amount of external light at the time when the tablet terminal is in use, which is detected with an optical sensor incorporated in the tablet terminal. The tablet terminal may include another detection device such as a sensor for detecting orientation (e.g., a gyroscope or an acceleration sensor) in addition to the optical sensor.

Although the display portion 9631*a* and the display portion 9631*b* have the same display area in FIG. 7A, one embodiment of the present invention is not limited to this example. The display portion 9631*a* and the display portion 9631*b* may have different areas or different display quality. For example, one of them may be a display panel that can display higher-definition images than the other.

FIG. 7B illustrates the tablet terminal folded, which includes the housing 9630, a solar battery 9633, a charge and discharge control circuit 9634, a battery 9635, and a DCDC converter 9636. Note that FIG. 7B shows an example in which the charge and discharge control circuit 9634 includes the battery 9635 and the DCDC converter 9636.

Since the tablet terminal can be folded in two, the housing 9630 can be closed when the tablet terminal is not in use. Thus, the display portions 9631*a* and 9631*b* can be protected, thereby providing a tablet terminal with high endurance and high reliability for long-term use.

The tablet terminal illustrated in FIGS. 7A and 7B can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs).

The solar battery 9633, which is attached on the surface of the tablet terminal, supplies electric power to a touch panel, a display portion, an image signal processor, and the like. Note that the solar battery 9633 can be provided on one or both surfaces of the housing 9630, so that the battery 9635 can be charged efficiently. When a lithium ion battery is used as the battery 9635, there is an advantage of downsizing or the like.

Figure 7C:
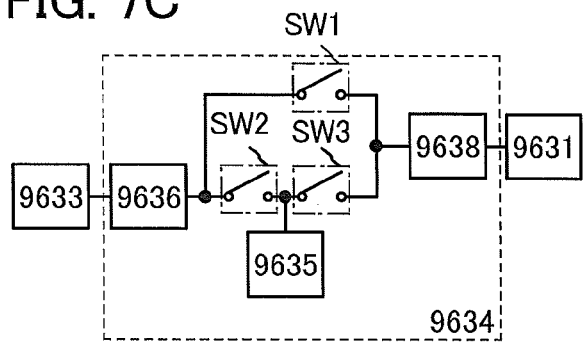

The structure and operation of the charge and discharge control circuit 9634 illustrated in FIG. 7B are described with reference to a block diagram of FIG. 7C. FIG. 7C illustrates the solar battery 9633, the battery 9635, the DCDC converter 9636, a converter 9638, switches SW1 to SW3, and the display portion 9631. The battery 9635, the DCDC converter 9636, the converter 9638, and the switches SW1 to SW3 correspond to the charge and discharge control circuit 9634 in FIG. 7B.

First, an example of operation in the case where power is generated by the solar battery 9633 using external light is described. The voltage of power generated by the solar battery 9633 is raised or lowered by the DCDC converter 9636 so that the power has a voltage for charging the battery 9635. When the display portion 9631 is operated with the power from the solar battery 9633, the switch SW1 is turned on and the voltage of the power is raised or lowered by the converter 9638 to a voltage needed for operating the display portion 9631. In addition, when display on the display portion 9631 is not performed, the switch SW1 is turned off and a switch SW2 is turned on so that charge of the battery 9635 may be performed.

Here, the solar battery 9633 is shown as an example of a power generation means; however, there is no particular limitation on a way of charging the battery 9635, and the battery 9635 may be charged with another power generation means such as a piezoelectric element or a thermoelectric conversion element (Peltier element). For example, the battery 9635 may be charged with a non-contact power transmission module that transmits and receives power wirelessly (without contact) to charge the battery or with a combination of other charging means.

It is needless to say that one embodiment of the present invention is not limited to the electronic device illustrated in FIGS. 7A to 7C as long as the display portion described in the above embodiment is included.

As described above, the electronic devices can be obtained by using the light-emitting device according to one embodiment of the present invention. Application range of the light-emitting device is so wide that the light-emitting device can be applied to electronic devices in a variety of fields.

Note that the structure described in this embodiment can be used in combination with any of the structures described in the other embodiments, as appropriate.

Embodiment 8

In this embodiment, examples of a lighting device in which a light-emitting device including a pyrazine derivative obtained by the synthesizing method of one embodiment of the present invention is used will be described with reference to FIG. 8.

Figure 8:
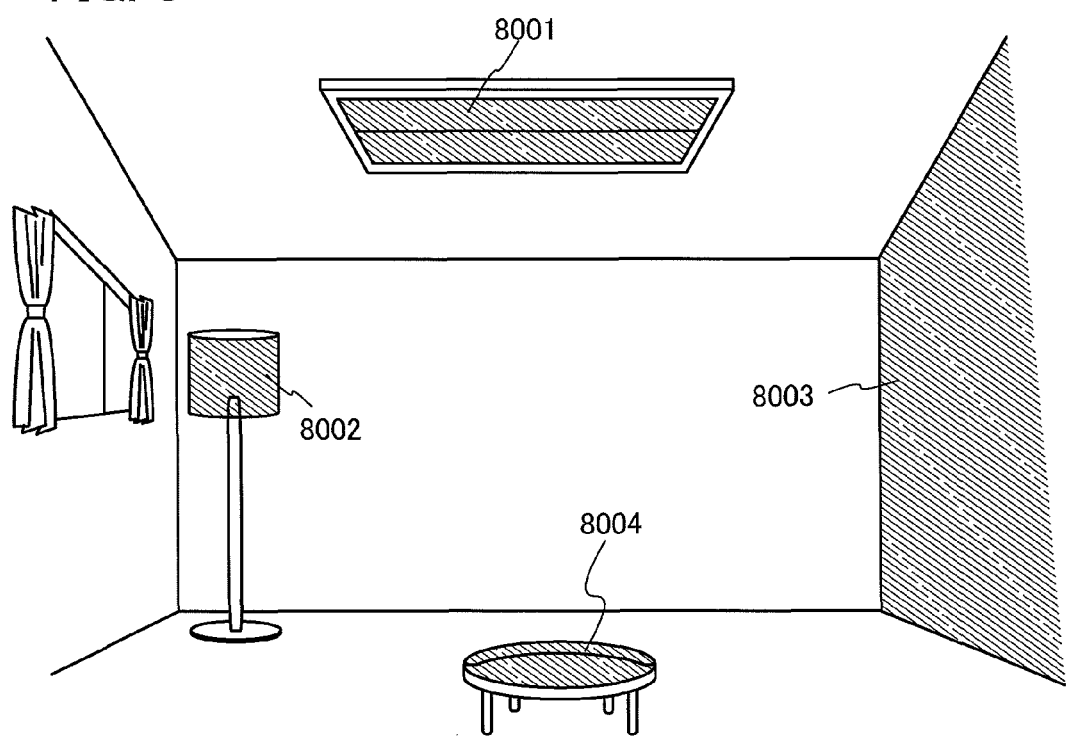
FIG. 8 illustrates lighting devices.

FIG. 8 illustrates an example in which the light-emitting device is used as an indoor lighting device 8001. Note that since the area of the light-emitting device can be increased, a lighting device having a large area can also be formed. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. Further, a wall of the room may be provided with a large lighting device 8003.

Moreover, when the light-emitting device is used for a table by being used as a surface of a table, a lighting device 8004 which has a function as a table can be obtained. When the light-emitting device is used as part of other furniture, a lighting device which has a function as the furniture can be obtained.

In this manner, a variety of lighting devices in which the light-emitting device is used can be obtained. Note that such lighting devices are also embodiments of the present invention.

Note that the structure described in this embodiment can be used in combination with any of the structures described in the other embodiments, as appropriate.

Example 1

Synthesis Example

In this example, a method of synthesizing 2-[3-(dibenzothiophen-4-yl)phenyl]dibenzo[f,h]quinoxaline (abbreviation: 2mDBTPDBq-II) (Structural Formula (101)) will be described as an example of the synthesizing method of one embodiment of the present invention. Note that a structure of 2mDBTPDBq-II (abbreviation) is shown below.

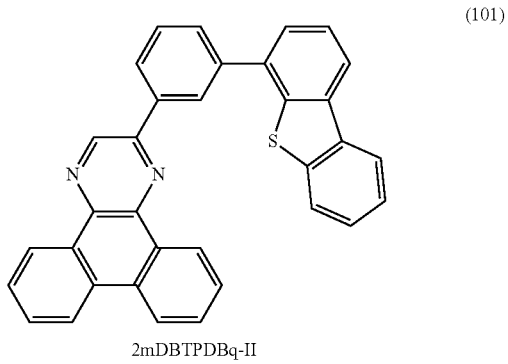 [SMILES: c1cc(-c2cnc3c4ccccc4c4ccccc4c3n2)cc(-c2cccc3c2sc2ccccc23)c1]

2mDBTPDBq-II

Step 1: Synthesis of 2-(3-bromophenyl)dibenzo[f,h]quinoxaline

First, into a 500-mL three-neck flask were put 2.5 g of 1-(3-bromophenyl)ethane-1,2-diamine, 0.62 g of potassium hydroxide, and 200 mL of dry ethanol, and the atmosphere in the flask was replaced with nitrogen. A reaction container was heated, the reacted solution was refluxed for two hours, 2.1 g of 9,10-phenanthrenequinone was added thereto, and the mixture was refluxed for nine hours. Then, the obtained mixture was subjected to suction filtration, and washed with ethanol, thereby obtaining 2-(3-bromophenyl)dibenzo[f,h]quinoxaline (a yellow white solid, a collection rate of 70%).

Synthesis Scheme (a-1) of Step 1 is shown below.

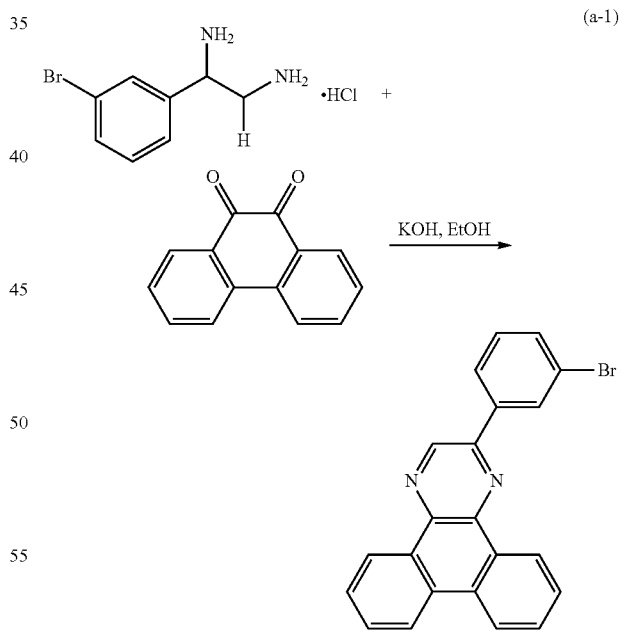

Step 2: Synthesis of 2-[3-(dibenzothiophen-4-yl)phenyl]dibenzo[f,h]quinoxaline (abbreviation: 2mDBTPDBq-II)

Next, into a 100-mL three-neck flask were put 1.3 g (3.4 mmol) of 2-(3-bromophenyl)dibenzo[f,h]quinoxaline obtained by Step 1, 0.78 g (3.5 mmol) of (dibenzothiophen- 4-yl)boronic acid, 0.10 g (0.068 mmol) of tris(2-methylphenyl)phosphine (abbreviation: P(o-toly)$_3$), 30 mL of toluene, 3.0 mL of ethanol, and 5.1 mL of a 2.0 M aqueous potassium carbonate solution. This mixture was degassed by being stirred under a reduced pressure, and the atmosphere in the flask was replaced with nitrogen.

Next, 15 mg (0.068 mmol) of palladium(II) acetate (abbreviation: Pd(OAc)$_2$) was added to this mixture. The mixture was stirred at 80° C. under a nitrogen stream for eight hours. After a predetermined time, the precipitated solid was separated by filtration to give a white solid. The obtained solid was washed with water and ethanol. Further, toluene was added thereto and the mixture was stirred while being heated, and then cooled down. This toluene solution was subjected to suction filtration, whereby 1.2 g of a white solid of 2-[3-(dibenzothiophen-4-yl)phenyl]dibenzo[f,h]quinoxaline (abbreviation: 2mDBTPDBq-II) was obtained at a collection rate of 74%.

Then, 1.2 g of the obtained white solid of 2-[3-(dibenzothiophen-4-yl)phenyl]dibenzo[f,h]quinoxaline (abbreviation: 2mDBTPDBq-II) was purified by a train sublimation method. The purification by sublimation was performed under such conditions that the pressure was 2.7 Pa, the flow rate of an argon gas was 5 mL/min, and 2-[3-(dibenzothiophen-4-yl)phenyl]dibenzo[f,h]quinoxaline was heated at 310° C. After the purification by sublimation, 0.77 g of a white powder of 2-[3-(dibenzothiophen-4-yl)phenyl]dibenzo[f,h]quinoxaline was obtained at a collection rate of 64%. Synthesis Scheme (a-2) of Step 2 is shown below.

Figure 9A:
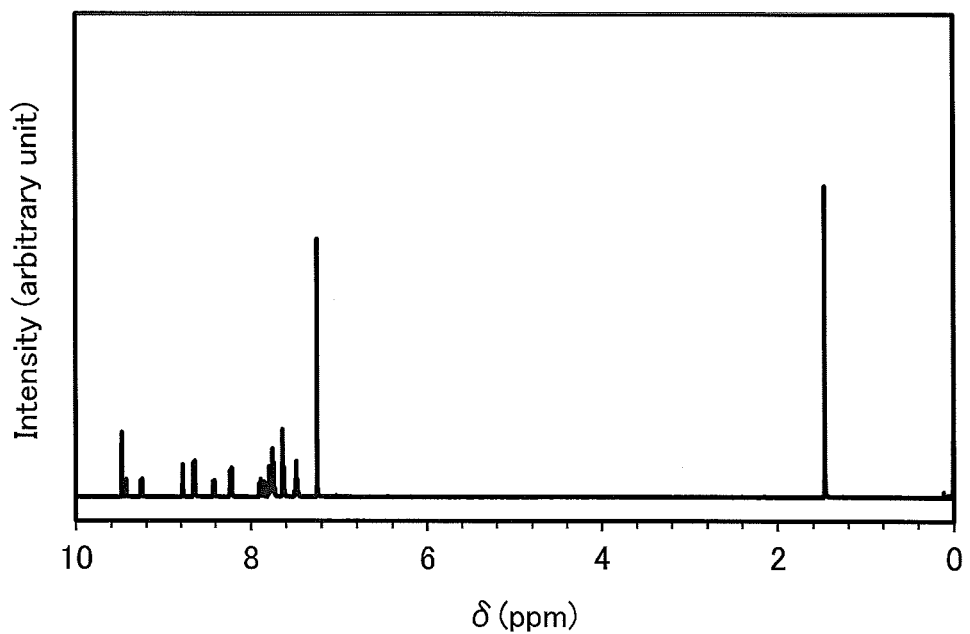
FIGS. 9A and 9B are $^1$H-NMR charts of an EL material represented by Structural Formula (101).
Figure 9B:
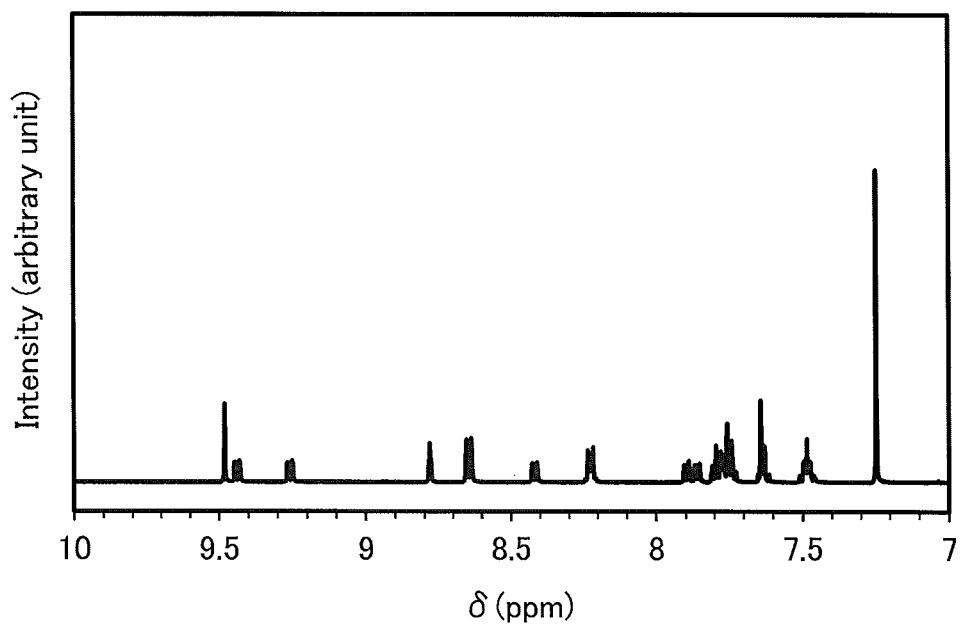

An analysis result by nuclear magnetic resonance ($^1$H-NMR) spectroscopy of the white powder obtained by Step 2 is described below. FIGS. 9A and 9B are $^1$H-NMR charts. FIG. 9B is an enlarged view of the chart in FIG. 9A whose lateral axis (δ) is within a range of 7 ppm to 10 ppm. These charts show that 2-[3-(dibenzothiophen-4-yl)phenyl]dibenzo[f,h]quinoxaline (abbreviation: 2mDBTPDBq-II) (Structural Formula (101)), which is a pyrazine derivative of one embodiment of the present invention, was obtained in this synthesis example.

$^1$H NMR. δ (500 MHz, CDCl$_3$): 7.44-7.50 (m, 2H), 7.60-7.61 (m, 2H), 7.67-7.87 (m, 7H), 8.17 (s, 1H), 8.19-8.22 (m, 2H), 8.34 (d, J=7.4 Hz, 2H), 8.77-8.78 (m, 1H), 9.23 (dd, J=7.2 Hz, 1.5 Hz, 1H), 9.42 (dd, J=7.8 Hz, 1.5 Hz, 1H), 9.48 (s, 1H).

Example 2

Figure 10:
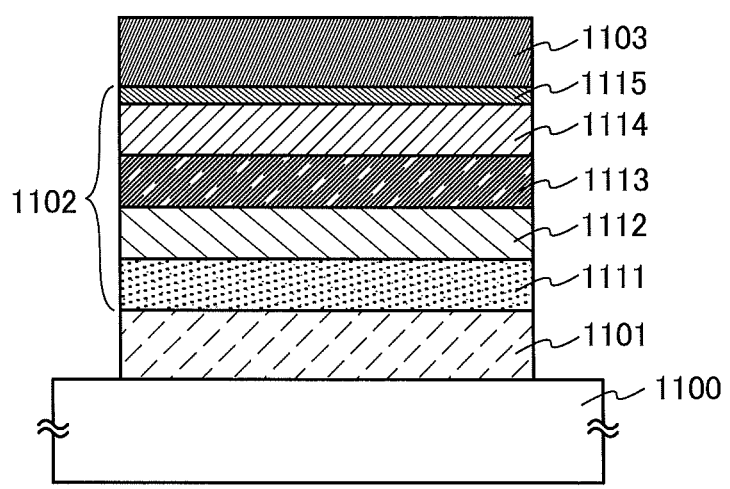
FIG. 10 illustrates structures of Light-emitting element 1 and Comparative light-emitting element 1.

In this example, Light-emitting element 1 which is one embodiment of the present invention and Comparative light-emitting element 1 formed for a comparison will be described with reference to FIG. 10. Note that chemical formulae of materials used in this example are shown below.

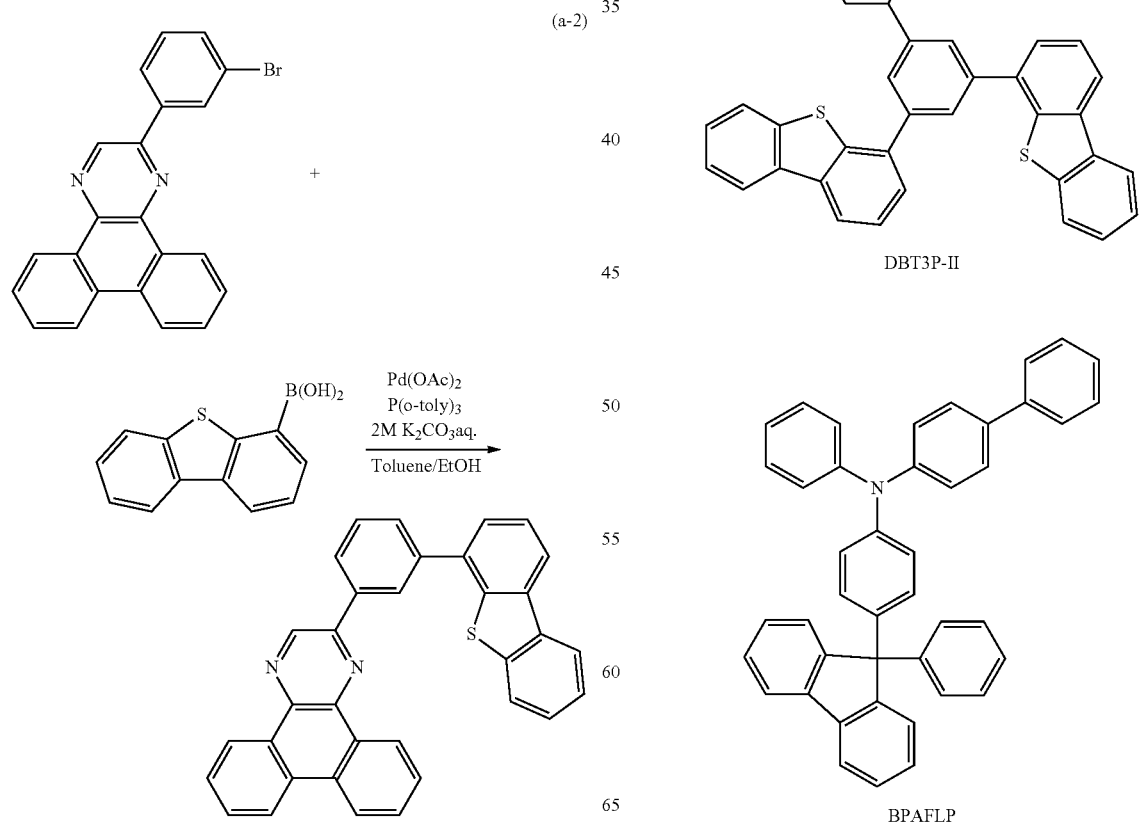

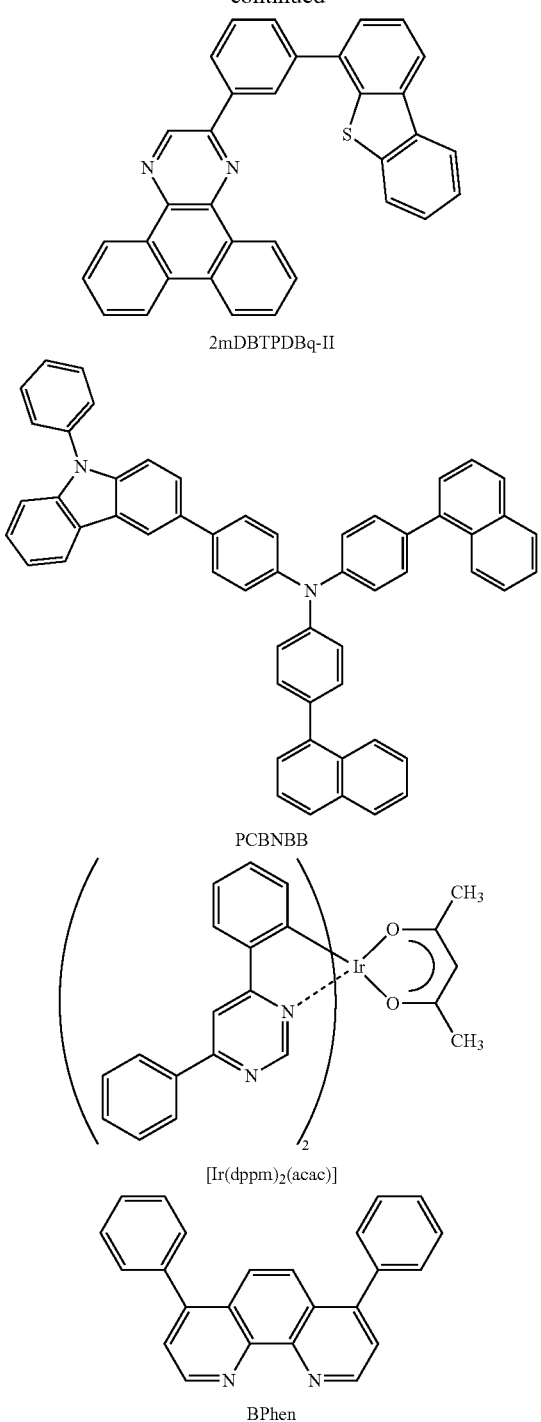

<<Formation of Light-Emitting Element 1 and Comparative Light-Emitting Element 1>>

First, indium tin oxide containing silicon oxide (ITSO) was deposited over a glass substrate 1100 by a sputtering method, so that a first electrode 1101 serving as an anode was formed. The thickness was 110 nm and the electrode area was 2 mm×2 mm.

Next, as pretreatment for forming Light-emitting element 1 and Comparative light-emitting element 1 over the substrate 1100, a surface of the substrate was washed with water, bak- ing was performed at 200° C. for one hour, and then UV ozone treatment was performed for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 on which the first electrode 1101 was formed faced downward. In this example, the case where the hole-injection layer 1111, the hole-transport layer 1112, the light-emitting layer 1113, the electron-transport layer 1114, and the electron-injection layer 1115 which are included in the EL layer 1102 are sequentially formed is described.

After reducing the pressure of the vacuum evaporation apparatus to $10^{-4}$ Pa, 1,3,5-tri(dibenzothiophen-4-yl)benzene (abbreviation: DBT3P-II) and molybdenum oxide were deposited by co-evaporation so that the mass ratio of DBT3P-II (abbreviation) to molybdenum oxide becomes 4:2, whereby the hole-injection layer 1111 was fainted over the first electrode 1101. The thickness of the hole injection layer 1111 was 40 nm. Note that a co-evaporation method is an evaporation method in which a plurality of different sub- stances is concurrently vaporized from respective different evaporation sources.

Then, 4-phenyl-4'-(9-phenylfluorene-9-yl)triphenylamine (abbreviation: BPAFLP) was evaporated to a thickness of 20 nm, so that the hole-transport layer 1112 was formed.

Next, the light-emitting layer 1113 was formed over the hole-transport layer 1112. The light-emitting layer 1113 with a thickness of 40 nm was formed by co-evaporation of 2-[3-(dibenzothiophen-4-yl)phenyl]dibenzo[f,h]quinoxaline (abbreviation: 2mDBTPDBq-II), 4,4'-di(1-naphthyl)-4''-(9-phenyl-9H-carbazol-3-yl)triphenylamine (abbreviation: PCBNBB), and (acetylacetonato)bis(4,6-diphenylpyrimidinato)iridium(III) (abbreviation: [Ir(dppm)$_2$(acac)]) at a mass ratio of 2mDBTPDBq-II to PCBNBB and [Ir(dppm)$_2$(acac)] of 0.8:0.2:0.05.

Then, 2mDBTPDBq-II (abbreviation) was evaporated to a thickness of 10 nm over the light-emitting layer 1113 and bathophenanthroline (abbreviation: Bphen) was evaporated to a thickness of 20 nm, whereby the electron-transport layer 1114 was formed. Furthermore, lithium fluoride was evaporated to a thickness of 1 nm over the electron-transport layer 1114, whereby the electron-injection layer 1115 was formed.

Note that 2mDBTPDBq-II (abbreviation) that was used for forming Light-emitting element 1 (the light-emitting layer 1113 and the electron-transport layer 1114) was synthesized by the synthesizing method of one embodiment of the present invention (specifically, the synthesizing method described in Example 1); on the other hand, 2mDBTPDBq-II (abbreviation) that was used for forming Comparative light-emitting element 1 was synthesized by a conventional synthesizing method. The conventional synthesizing method is described at the end of this example as a reference synthesis example.

Finally, aluminum was evaporated to a thickness of 200 nm over the electron-injection layer 1115 to form a second electrode 1103 serving as a cathode; thus, Light-emitting element 1 and Comparative light-emitting element 1 were obtained. Note that, in the above evaporation process, evaporation was all performed by a resistance heating method.

Element structures of Light-emitting element 1 and Comparative light-emitting element 1 obtained as described above are shown in Table 1.

TABLE 1

|  | First electrode | Hole-injection layer | Hole-transport layer | Light-emitting layer | Eectron-transport layer | | Electron-injection layer | Second electrode |
|---|---|---|---|---|---|---|---|---|
| Light-emitting element 1 | ITSO (110 nm) | DBT3P-II:MoOx (4:2 40 nm) | BPAFLP (20 nm) | * | 2mDBTPDBq-II (synthesizing method of the present invention) (10 nm) | Bphen (20 nm) | LiF (1 nm) | Al (200 nm) |
| Comparative light-emitting element 1 | ITSO (110 nm) | DBT3P-II:MoOx (4:2 40 nm) | BPAFLP (20 nm) | ** | 2mDBTPDBq-II (conventional synthesizing method) (10 nm) | Bphen (20 nm) | LiF (1 nm) | Al (200 nm) |

* 2mDBTPDBq-II (synthesizing method of the present invention):PCBNBB:[Ir(dppm)2(acac)] (0.8:0.2:0.05 40 nm)
** 2mDBTPDBq-II (conventional synthesizing method):PCBNBB:[Ir(dppm)2(acac)] (0.8:0.2:0.05 40 nm)

After the formation, each of Light-emitting element 1 and Comparative light-emitting element 1 was sealed in a glove box containing a nitrogen atmosphere so as not to be exposed to the air (specifically, a sealant was applied onto an outer edge of the element and heat treatment was performed at 80° C. for one hour at the time of sealing).

<<Operation Characteristics of Light-Emitting Element 1 and Comparative Light-Emitting Element 1>>

Operation characteristics of the formed Light-emitting element 1 and Comparative light-emitting element 1 were measured. Note that the measurement was carried out at room temperature (in an atmosphere kept at 25° C.).

Figure 11:
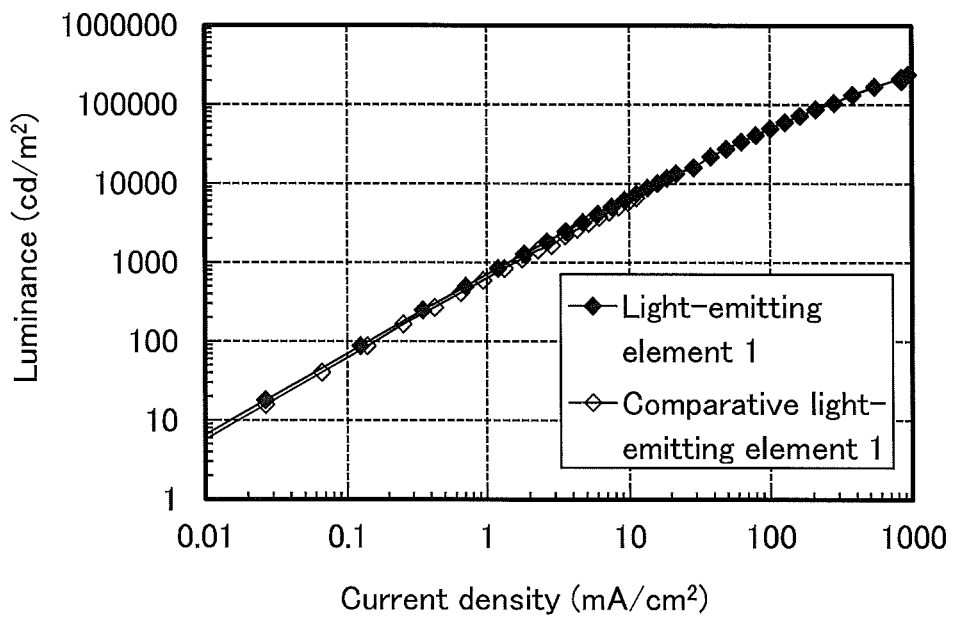
FIG. 11 shows current density-luminance characteristics of Light-emitting element 1 and Comparative light-emitting element 1.
Figure 12:
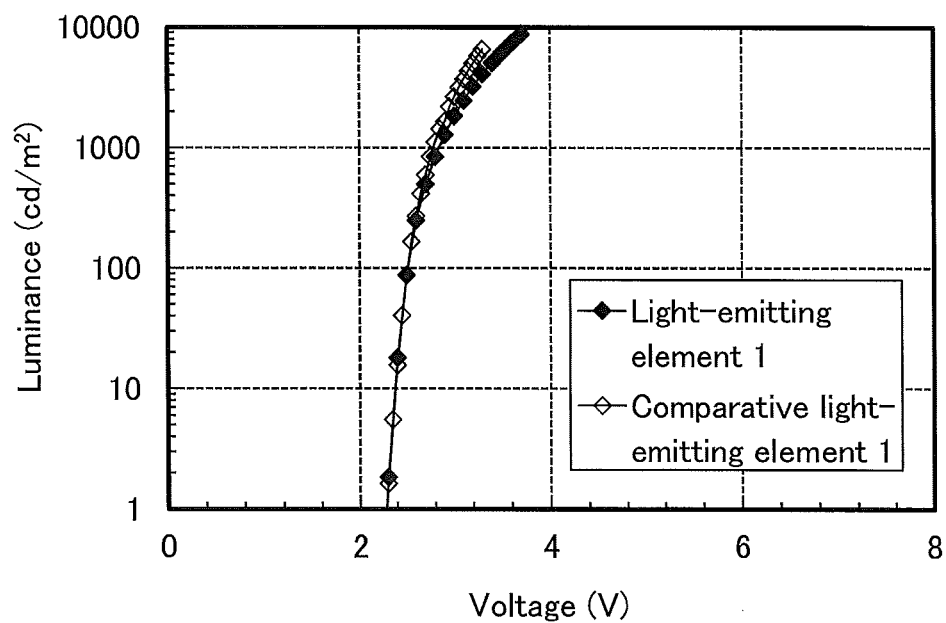
FIG. 12 shows voltage-luminance characteristics of Light-emitting element 1 and Comparative light-emitting element 1.

FIG. 11 shows current density-luminance characteristics of Light-emitting element 1 and Comparative light-emitting element 1. In FIG. 11, the vertical axis represents luminance (cd/m$^2$) and the lateral axis represents current density (mA/cm$^2$). FIG. 12 shows voltage-luminance characteristics of Light-emitting element 1 and Comparative light-emitting element 1. In FIG. 12, the vertical axis represents luminance (cd/m$^2$) and the lateral axis represents voltage (V).

Table 2 below shows initial values of main characteristics of Light-emitting element 1 and Comparative light-emitting element 1 at a luminance of about 1000 cd/m$^2$. From each of the light-emitting elements, orange light emission originating from [Ir(dppm)$_2$(acac)] was obtained.

TABLE 2

|  | Voltage (V) | Current (mA) | Current density (mA/cm$^2$) | Lumimance (cd/m$^2$) | Current efficiency (cd/A) | Power efficiency (lm/W) |
|---|---|---|---|---|---|---|
| Light-emitting element 1 | 2.8 | 0.048 | 1.2 | 840 | 70 | 79 |
| Comparative light-emitting element 1 | 2.8 | 0.07 | 1.8 | 1100 | 63 | 71 |

Figure 13:
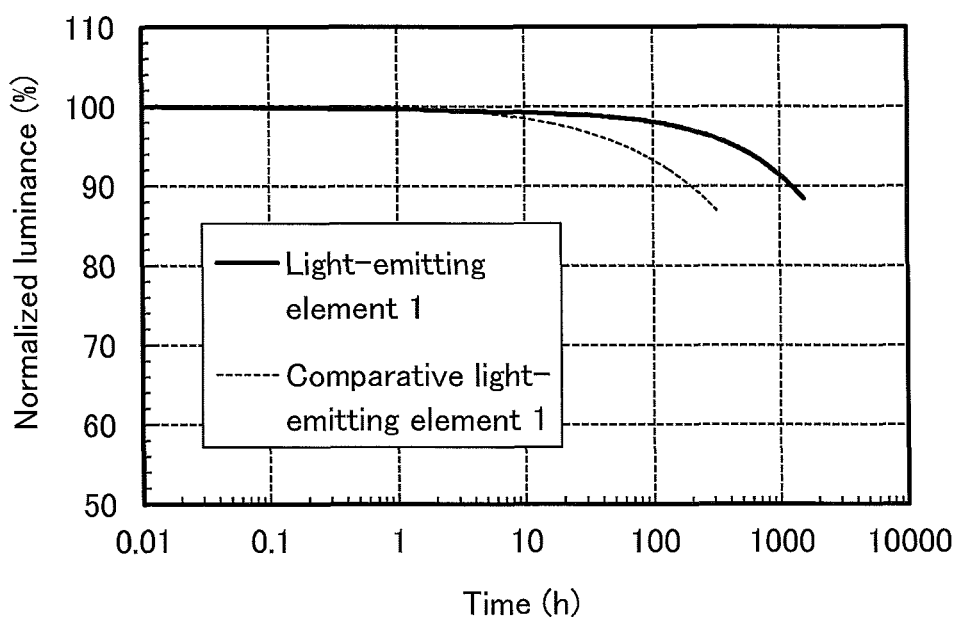
FIG. 13 shows reliability of each of Light-emitting element 1 and Comparative light-emitting element 1.

FIG. 13 shows the results of reliability tests on Light-emitting element 1 and Comparative light-emitting element 1. In FIG. 13, the vertical axis represents normalized luminance (%) with an initial luminance of 100% and the lateral axis represents driving time (h) of the element. Note that in the reliability tests, Light-emitting element 1 and Comparative light-emitting element were driven under the conditions that the initial luminance was set to 5000 cd/m$^2$ and the current density was constant. As a result, the luminance of Comparative light-emitting element 1 after 100-hour driving was about 93% of the initial luminance; on the other hand, the luminance of Light-emitting element 1 after 100-hour driving was about 98% of the initial luminance.

Note that in Light-emitting element 1, 2mDBTPDBq-II (abbreviation) synthesized by the synthesizing method of one embodiment of the present invention, that is, the method of synthesizing a pyrazine derivative without a synthetic pathway of a pyrazine halide derivative, which is a synthetic intermediate, whose pytazine skeleton is halogenated, is used as an EL material in an EL layer. On the other hand, in Comparative light-emitting element 1, 2mDBTPDBq-II (abbreviation) synthesized by a conventional synthesizing method described later in this example is used as an EL material in an EL layer. The results show that Light-emitting element 1 in which the pyrazine derivative obtained by the synthesizing method of one embodiment of the present invention is used as the EL material has higher reliability and a longer lifetime than Comparative light-emitting element 1.

(Reference Synthesizing Method: Conventional Synthesizing Method)

As a reference synthesizing method, description is given below of the conventional method of synthesizing 2-[3-(dibenzothiophen-4-yl)phenyl]dibenzo[f,h]quinoxaline (abbreviation: 2mDBTPDBq-II) represented by Structural Formula (101).

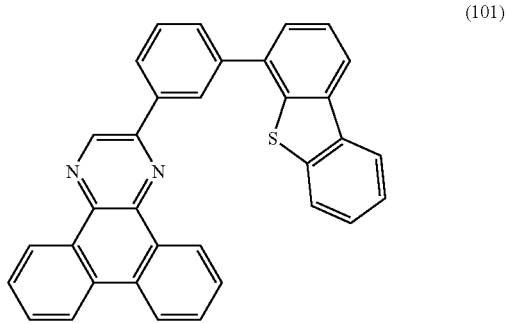 [SMILES: c1cc(-c2cnc3c4ccccc4c4ccccc4c3n2)cc(-c2cccc3c2sc2ccccc23)c1]

(101)

<<Synthesis of 2mDBTPDBq-II>>
Synthesis Scheme (b-1) of 2mDBTPDBq-II is shown.

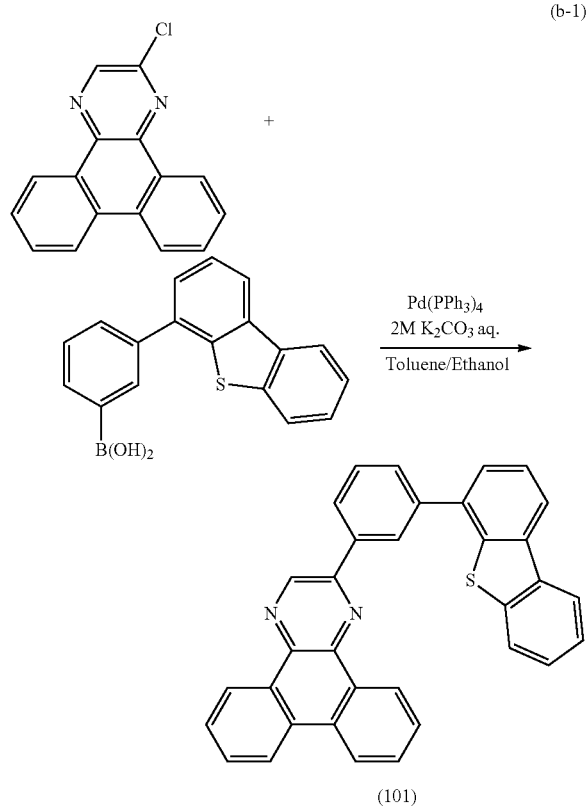

Into a 2-L three-neck flask were put 5.3 g (20 mmol) of 2-chlorodibenzo[f,h]quinoxaline, 6.1 g (20 mmol) of 3-(dibenzothiophen-4-yl)phenylboronic acid, 460 mg (0.4 mmol) of tetrakis(triphenylphosphine)palladium(0), 300 mL of toluene, 20 mL of ethanol, and 20 mL of a 2M aqueous solution of potassium carbonate. The mixture was degassed by being stirred under a reduced pressure, and the atmosphere in the flask was replaced with nitrogen. This mixture was stirred under a nitrogen stream at 100° C. for 7.5 hours. After cooled to room temperature, the obtained mixture was filtered to give a white substance. The obtained substance by the filtration was washed with water and ethanol in this order, and then dried. The obtained solid was dissolved in about 600 mL of hot toluene, followed by suction filtration through Celite (produced by Wako Pure Chemical Industries, Ltd., Catalog No. 531-16855) and Florisil (produced by Wako Pure Chemical Industries, Ltd., Catalog No. 540-00135), whereby a clear colorless filtrate was obtained. The obtained filtrate was concentrated and purified by silica gel column chromatography. The chromatography was carried out using hot toluene as a developing solvent. Acetone and ethanol were added to the solid obtained here, followed by irradiation with ultrasonic waves. Then, the generated suspended solid was filtered and the obtained solid was dried, whereby 7.85 g of a white powder of a target substance was obtained at a collection rate of 80%.

Here, the purity analysis of 2-chlorodibenzo[f,h]quinoxaline, which is a source material, was performed by ACQUITY Ultra Performance LC (hereinafter referred to as UPLC). From the analysis, an area ratio of the areas except 2-chlorodibenzo[f,h]quinoxaline was calculated that a detected mass m/z=232 was 0.4% and m/z=299 was 0.9%, so that the purity was 98.7%. These impurities are thought to be dibenzo [f,h]quinoxaline and 2-chlorodibenzo[f,h]quinoxaline monosubstituted by chlorine (Structural Formula (102)). Structural Formula (102) is shown below. In this way, the pyrazine halide derivative (General Formula (B1)) described in Embodiment 1 generally contains the dihalide represented by (General Formula (B1')) as an impurity.

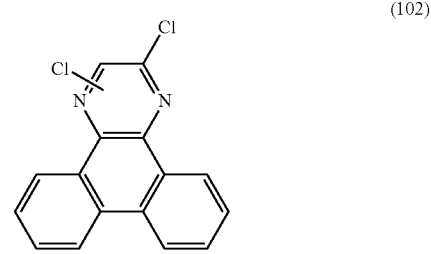

Next, purification of the target substance (2mDBTPDBq-II (abbreviation)) was performed. The target substance was relatively soluble in hot toluene, but was easy to precipitate when cooled. Furthermore, the substance was poorly soluble in other organic solvents such as acetone and ethanol. Hence, the utilization of these different degrees of solubility resulted in a high-yield synthesis by a simple method as above. Specifically, after the reaction, the mixture was returned to room temperature and the precipitated solid was collected by filtration, whereby most impurities were able to be easily removed. Furthermore, by the column chromatography with hot toluene as a developing solvent, the target substance, which is easy to precipitate, was able to be readily purified.

By a train sublimation method, 4.0 g of the obtained white powder was purified. In the purification, the white powder was heated at 300° C. under a pressure of 5.0 Pa with a flow rate of argon gas of 5 mL/min After the purification, 3.5 g of a white powder of a target substance was obtained at a collection rate of 88%.

The purity analysis of 2mDBTPDBq-II (abbreviation) obtained by the above synthesis and purification methods was performed by UPLC (high performance liquid chromatography). In this analysis, an impurity was detected at m/z=523. To measure the concentration of a halogen element contained in 2mDBTPDBq-II (abbreviation), quantification of chlorine was performed by a combustion-ion chromatography method, so that 32 ppm of chlorine was detected. From these results, this impurity is thought to be a monochloro (Structural Formula (103)) of 2mDBTPDBq-II (abbreviation). The structure of Structural Formula (103) is shown below. The above results show that 2-chlorodibenzo[f,h]quinoxaline monosubstituted by chlorine (Structural Formula (102)), which is contained in the source material, reacts with one equivalent of a boronic acid, so that the EL material (2mDBT-PDBq-II (abbreviation) that is a target substance) containing chlorine as a substituent remains as an impurity. Data of Comparative light-emitting element 1 suggests that the EL material containing chlorine as a substituent adversely affects the reliability of the element.

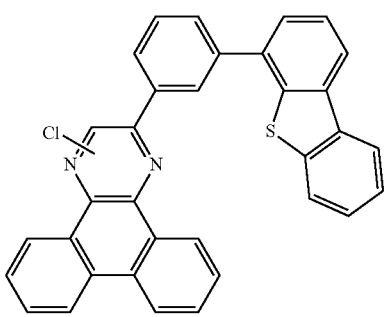

(103)

Therefore, it was found that when the reaction shown in Synthesis Scheme (B-2) is performed using the pyrazine halide derivative (General Formula (B1)) containing the impurity (General Formula (B1')) as described in the above embodiment, the impurity (General Formula (G1')) that is a halogen body of the target substance (General Formula (G1)) is generated as shown in Synthesis Scheme (B-2'). Moreover, such an impurity (General Formula (G1')) adversely affects the reliability of the light-emitting element to a great extent.

Example 3

Synthesis Example

In this example, a method of synthesizing 2-[3'-(dibenzothiophen-4-yl)biphenyl-3-yl]dibenzo[f,h]quinoxaline (abbreviation: 2mDBTBPDBq-II) (Structural Formula (102)) will be described as an example of the synthesizing method of one embodiment of the present invention. Note that a structure of 2mDBTBPDBq-II (abbreviation) is shown below.

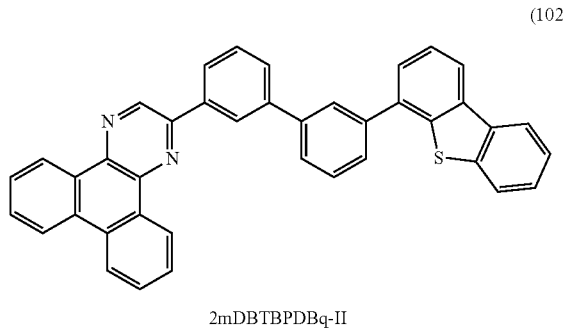

(102)

2mDBTBPDBq-II

Step 1: Synthesis of (3-bromophenyl)dibenzothiophene

First, into a 50.0-L reactor vessel were put 1870 g (6.60 mol) of 3-bromoiodobenzene, 1370 g (6.00 mol) of dibenzothiophene-4-boronic acid, 18.3 g (60.0 mmol) of tri(orthotolyl)phosphine (abbreviation: P(o-tolyl)$_3$), 1660 g (12.0 mol) of potassium carbonate, 6.00 L of water, 20.0 L of toluene, 10.0 L of ethanol, and 6.74 g (30.0 mmol) of palladium(II) acetate (abbreviation: Pd(OAc)$_2$), and the atmosphere in the reactor vessel was replaced with nitrogen.

This mixture was degassed by being stirred while the pressure was reduced. The obtained mixture was stirred under a nitrogen stream at 75° C. for two hours. After the stirring, an aqueous layer was removed from the mixture, the organic layer was subjected to suction filtration, so that a filtrate was obtained. To an oily substance obtained by concentrating the filtrate was added about 2.00 L of toluene. While 47.0 L of hexane in a 50.0-L reactor vessel was being stirred, the solution was dropped thereto with a dropping funnel at a rate of 200 mL/min, so that a solid was precipitated. The precipitated solid was collected by suction filtration, combined with a solid obtained by concentrating the filtrate, and were washed with about 4.50 L of toluene.

After the washing, the solid was put into a 50.0-L reactor vessel, 10.0 L of ethanol was added thereto, and the mixture was heated at 80° C. while being stirred, so that the solid was dissolved. The mixture was left still at the same temperature for 30 minutes to separate into two layers. The upper layer of the mixture was cooled with ice to be recrystallized, so that a solid was obtained. The obtained solid was washed with about 2.00 L of hexane, so that 558 g of a white powder of a target substance was obtained. The lower layer resulted from the separation into two layers was cooled down to the room temperature to give a brown solid, and the brown solid was recrystallized with 2.60 L of ethanol, so that a solid was obtained. The obtained solid was washed with 1.5 L of hexane to give 267 g of a light-brown powder of a target substance. The target substance was 825 g in total, and the collection rate was 41%.

Synthesis Scheme (b-1) of Step 1 is shown below.

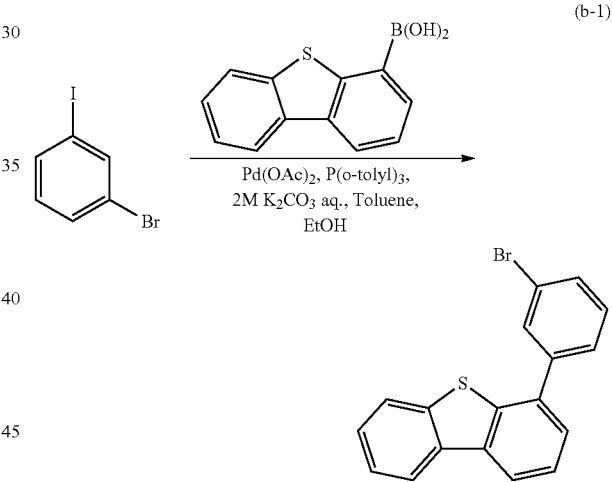

(b-1)

Step 2: Synthesis of 3-(dibenzothiophen-4-yl)phenylboronic acid

Next, into a 50.0-L reactor vessel was put 720 g (2.20 mol) of 4-(3-bromophenyl)dibenzothiophene obtained in Step 1 described above, and the atmosphere in the reactor vessel was replaced with argon. Into the reactor vessel, 18 L of dehydrated tetrahydrofuran (THF) was added, and the solution was cooled down to −80° C. Then, 1.50 L (2.40 mol) of n-butyllithium (1.6 mol/L of an n-hexane solution) was dropped to the solution with a dropping funnel at a rate of 20 mL/min.

After the dropping, the solution was stirred for three hours while its temperature was increased to −60° C. After the stirring, the solution was cooled down to −80° C., and 265 g (2.50 mol) of trimethyl borate was added to the solution, followed by stirring for 15 hours while its temperature was returned to room temperature. After the stirring, 3.00 L of dilute hydrochloric acid (1.0 mol/L) was added to the solution, followed by stirring for two hours. After the stirring, an aqueous layer of this mixture was extracted with ethyl acetate. The obtained solution of the extract was combined with an organic layer and then washed with a saturated sodium hydrogen carbonate solution. The organic layer was dried with magnesium sulfate. After the drying, the mixture was subjected to gravity filtration. The obtained filtrate was concentrated to give an oily substance. To the obtained oily substance was added 5.00 L of toluene and concentration was performed again on the mixture, so that a solid was obtained. The obtained solid was washed with ice-cooled toluene to give 472 g of a white powder of a target substance at a collection rate of 73%. Synthesis Scheme (b-2) of Step 2 is shown below.

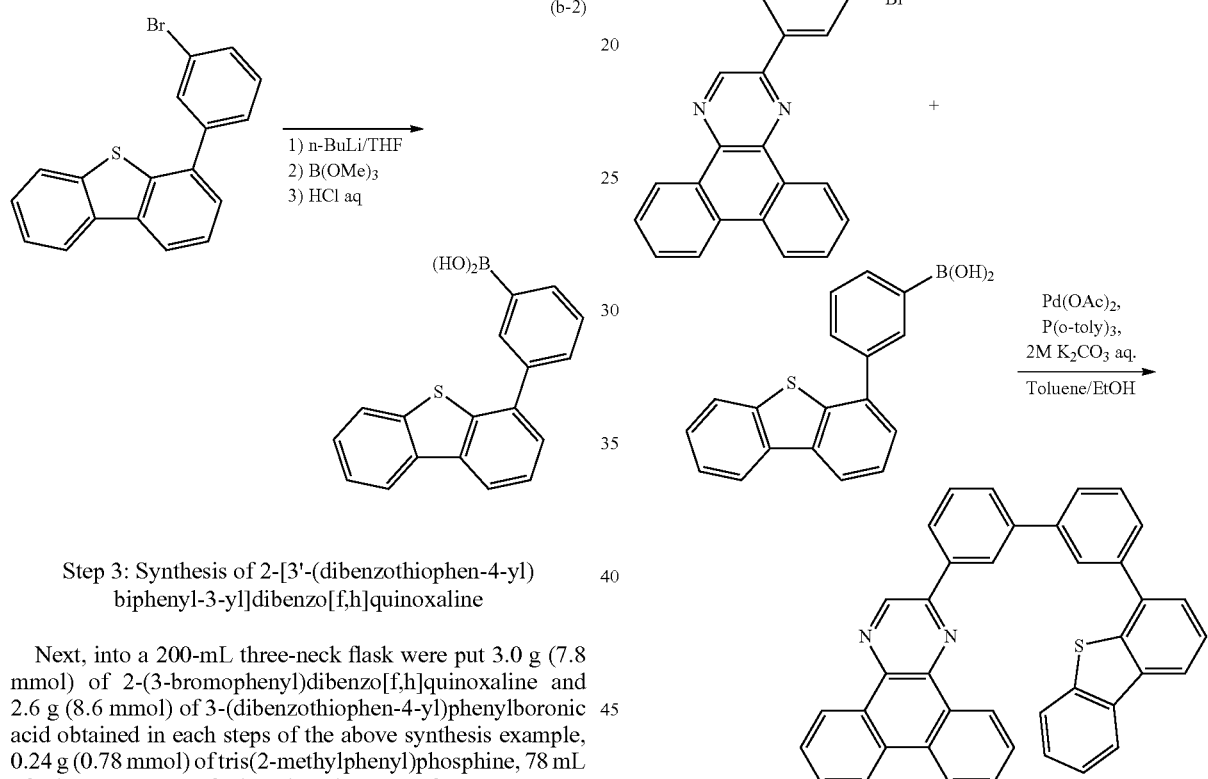

Step 3: Synthesis of 2-[3'-(dibenzothiophen-4-yl)biphenyl-3-yl]dibenzo[f,h]quinoxaline Next, into a 200-mL three-neck flask were put 3.0 g (7.8 mmol) of 2-(3-bromophenyl)dibenzo[f,h]quinoxaline and 2.6 g (8.6 mmol) of 3-(dibenzothiophen-4-yl)phenylboronic acid obtained in each steps of the above synthesis example, 0.24 g (0.78 mmol) of tris(2-methylphenyl)phosphine, 78 mL of toluene, 7.8 mL of ethanol, and 12 mL of 2.0 M aqueous potassium carbonate solution.

This mixture was degassed by being stirred under a reduced pressure and the atmosphere in the flask was replaced with nitrogen. To the mixture was added 35 mg (0.16 mmol) of palladium(II) acetate, and the mixture was stirred under a nitrogen stream at 80° C. for eight hours. After a predetermined time, the precipitated solid was separated by filtration to give a yellow solid. The solid was washed with water and ethanol, toluene was added thereto, and the mixture was stirred while being heated. The toluene solution was subjected to suction filtration, whereby 2.7 g of a yellow solid was obtained at a collection rate of 61%.

Then, 2.7 g of the obtained yellow powder of 2-[3'-(dibenzothiophen-4-yl)biphenyl-3-yl]dibenzo[f,h]quinoxaline was purified by a train sublimation method. The purification was performed such that 2-[3'-(dibenzothiophen-4-yl)biphenyl-3-yl]dibenzo[f,h]quinoxaline was heated at 320° C. under conditions that the pressure was 2.7 Pa and the flow rate of an argon gas was 15 mL/min. After the purification by sublimation, 2.3 g of a yellow powder of 2-[3'-(dibenzothiophen-4-yl)biphenyl-3-yl]dibenzo[f,h]quinoxaline was obtained at a collection rate of 85%.

Then, 2.3 g of the obtained yellow powder of 2-[3'-(dibenzothiophen-4-yl)biphenyl-3-yl]dibenzo[f,h]quinoxaline was purified by a train sublimation method. The purification was performed such that 2-[3-(dibenzothiophen-4-yl)phenyl]dibenzo[f,h]quinoline was heated at 320° C. under conditions that the pressure was 2.7 Pa and the flow rate of an argon gas was 15 mL/min. After the purification, 1.7 g of a white powder of 2-[3'-(dibenzothiophen-4-yl)biphenyl-3-yl]dibenzo[f,h]quinoxaline was obtained at a collection rate of 74%. Synthesis Scheme (b-3) of Step 3 is shown below.

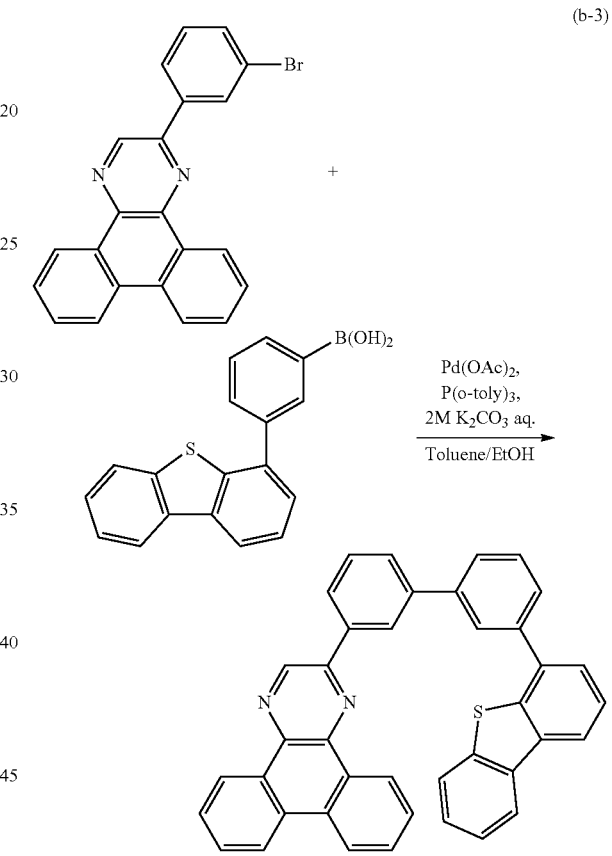

Figure 14A:
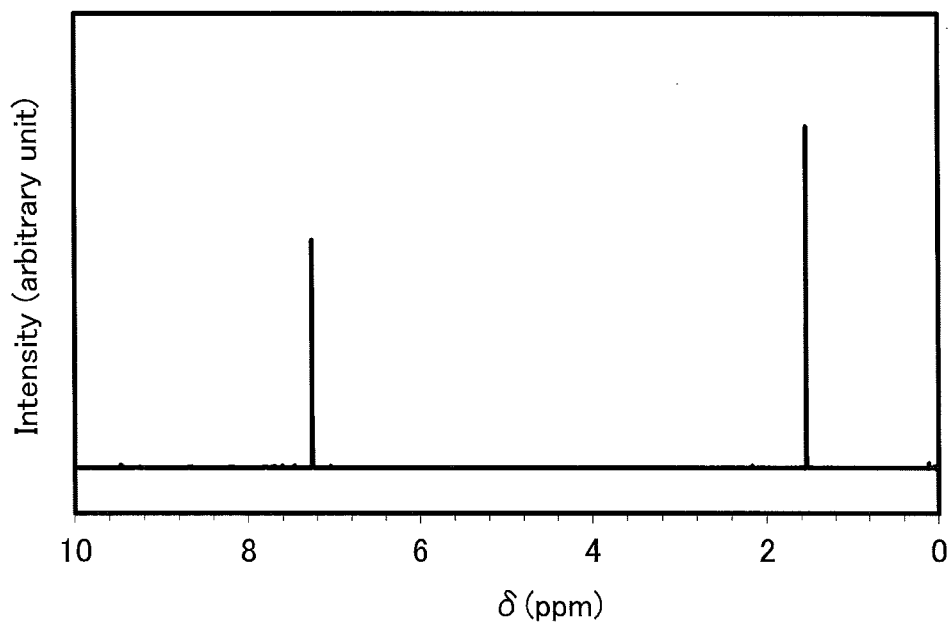
FIGS. 14A and 14B are $^1$H-NMR charts of an EL material represented by Structural Formula (102).
Figure 14B:
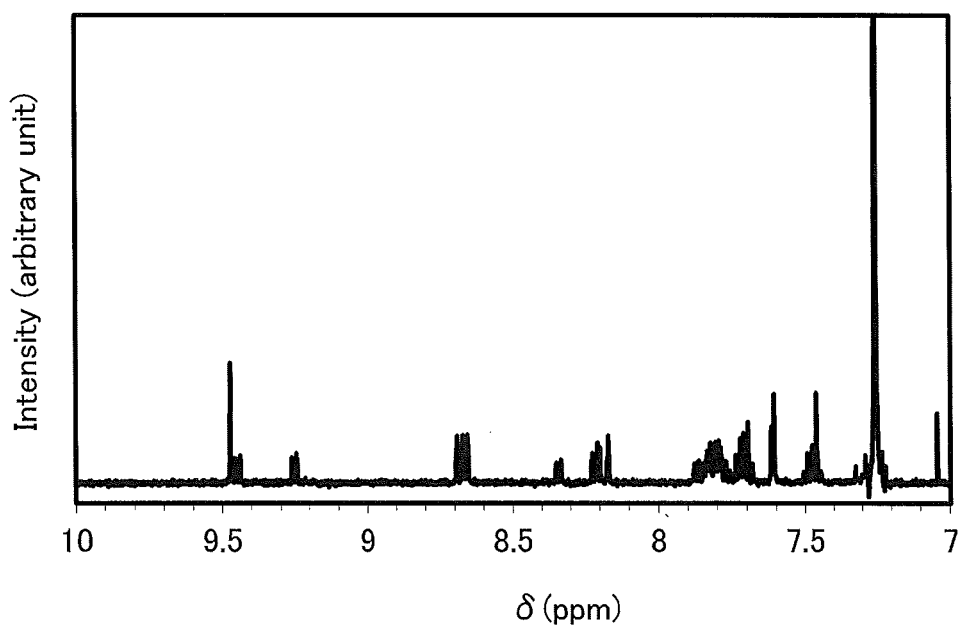

An analysis result by nuclear magnetic resonance ($^1$H-NMR) spectroscopy of the white powder obtained by Step 3 is described below. FIGS. 14A and 14B are $^1$H-NMR charts. FIG. 14B is an enlarged view of the chart in FIG. 14A whose lateral axis (δ) is within a range of 7 ppm to 10 ppm. These charts show that 2-[3'-(dibenzothiophen-4-yl)biphenyl-3-yl]dibenzo[f,h]quinoxaline (abbreviation: 2mDBTBPDBq-II) (Structural Formula (102)), which is a pyrazine derivative of one embodiment of the present invention, was obtained in this synthesis example.

$^1$H NMR. δ (500 MHz, CDCl$_3$): δ=7.46-7.51 (m, 2H), 7.61-7.65 (m, 2H), 7.73-7.81 (m, 5H), 7.85-7.90 (m, 1H), 7.90 (d, H), 8.66 (d, J=8.0 Hz, 2H), 8.69 (s, 1H), 9.27 (dd, J=7.5 Hz, 1.7 Hz, 1H), 9.45 (d, J=8.0 Hz, 1H), 9.47 (s, 1H).

This application is based on Japanese Patent Application serial no. 2012-125869 filed with Japan Patent Office on Jun. 1, 2012, the entire contents of which are hereby incorporated by reference.

What is claimed is:

1. A method comprising the step of cyclizing an α-diketone and a 1-(haloaryl)ethane-1,2-diamine derivative to form a 2-(haloaryl)pyrazine derivative,
wherein the α-diketone is any one of glyoxal, 1-phenyl glyoxal, benzil, and 9,10-phenanthrenequinone in which phenyl groups of benzil are bonded to each other at the ortho position,
wherein the 1-(haloaryl)ethane-1,2-diamine derivative is represented by a formula (A1),

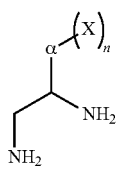

(A1)

wherein α represents an aryl group,
wherein X represents halogen, and
wherein n is any of 1 to 3.

2. The method according to claim 1, wherein the 2-(haloaryl)pyrazine derivative is represented by a formula (G0),

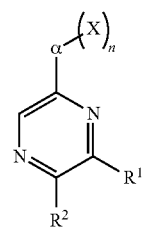

(G0)

wherein α represents an aryl group,
wherein X represents halogen,
wherein n is any of 1 to 3, and
wherein $R^1$ and $R^2$ each independently represent hydrogen or a phenyl group.

3. The method according to claim 1,
wherein the 2-(haloaryl)pyrazine derivative is represented by a formula (G0),

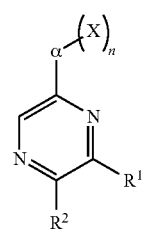

(G0)

wherein α represents an aryl group,
wherein X represents halogen,
wherein n is any of 1 to 3, and
wherein $R^1$ and $R^2$ are bonded to each other to form a phenanthrene ring.

4. The method according to claim 1, wherein the α-diketone is represented by a formula (A2),

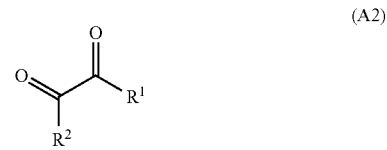

(A2)

wherein $R^1$ and $R^2$ each independently represent hydrogen or a phenyl group.

5. A method comprising the steps of:
cyclizing an α-diketone and a 1-(haloaryl)ethane-1,2-diamine derivative to form a 2-(haloaryl)pyrazine derivative; and
coupling the 2-(haloaryl)pyrazine derivative and an arylboronic acid or a heteroarylboronic acid to form a 2-arylpyrazine derivative comprising an aryl group or a heteroaryl group,
wherein the α-diketone is any one of glyoxal, 1-phenyl glyoxal, benzil, and 9,10-phenanthrenequinone in which phenyl groups of benzil are bonded to each other at the ortho position,
wherein the 1-(haloaryl)ethane-1,2-diamine derivative is represented by a formula (A1),

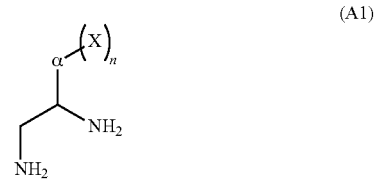

(A1)

wherein α represents an aryl group,
wherein X represents halogen, and
wherein n is any of 1 to 3.

6. The method according to claim 5, wherein the 2-arylpyrazine derivative is represented by a formula (G1),

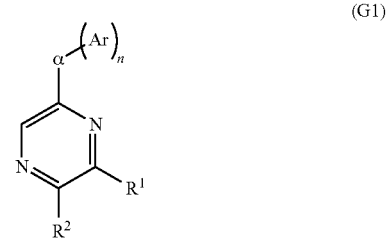

(G1)

wherein α represents an aryl group,
wherein X represents halogen,
wherein n is any of 1 to 3, and
wherein $R^1$ and $R^2$ each independently represent hydrogen, an alkyl group, or a phenyl group.

7. The method according to claim 5,
wherein the 2-(haloaryl)pyrazine derivative is represented by a formula (G0),

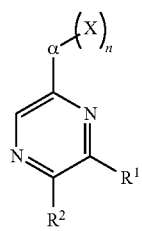

(G0)

wherein α represents an aryl group, wherein X represents halogen, wherein n is any of 1 to 3, and wherein $R^1$ and $R^2$ are bonded to each other to form a phenanthrene ring.

8. The method according to claim 5, wherein the 2-arylpyrazine derivative is represented by a formula (101),

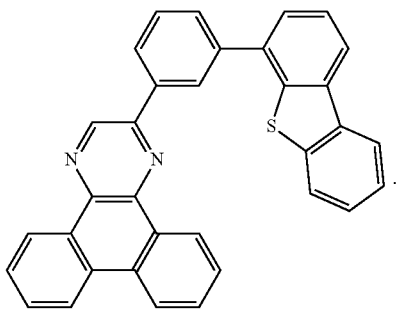

(101)

9. The method according to claim 1, wherein the α-diketone is 9,10-phenanthrenequinone.

10. The method according to claim 5, wherein the α-diketone is 9,10-phenanthrenequinone.

* * * * *

UNITED STATES PATENT AND TRADEMARK OFFICE
CERTIFICATE OF CORRECTION

Page 1 of 2

PATENT NO. : 9,196,844 B2
APPLICATION NO. : 13/905829
DATED : November 24, 2015
INVENTOR(S) : Hideko Inoue et al.

It is certified that error appears in the above-identified patent and that said Letters Patent is hereby corrected as shown below:

In the Specification:

Column 3, Line 57; Change "a represents" to --α represents--.

Column 6, Line 2; Change "(B2')" to --(B-2')--.

Column 8, Line 64; Change "dibenzo quinoxaline" to --dibenzo[f,h]quinoxaline--.

Column 9, Line 14; Change "Alq$_a$," to --Alq$_3$,--.

Column 12, Line 25; Change "n-electron" to --π-electron--.

Column 12, Line 50; Change "N,N-diphenylbenzene" to --N,N'-diphenylbenzene--.

Column 12, Line 58; Change "N,N-diphenyl" to --N,N'-diphenyl--.

Column 12, Line 63; Change "[N-phenyl-N-(" to --[N'-phenyl-N'-(--.

Column 13, Line 4; Change ")-N-phenylamino]" to --)-N'-phenylamino]--.

Column 13, Line 5; Change "DNIPD)," to --DNTPD),--.

Column 13, Line 63; Change "p-channel T or both." to --p-channel TFT or both.--.

Column 14, Line 43; Change "tennis" to --terms--.

Column 16, Line 30; Change "410E" to --410G,--.

Column 16, Line 36; Change "404E" to --404G,--.

Column 16, Line 52; Change "(4)" to --($\lambda_B$)--.

Column 16, Line 56; Change "(4)" to --($\lambda_R$)--.

Column 16, Line 60; Change "410E" to --410G,--.

Column 18, Line 62; Change "404G respectively." to --404G, respectively.--.

Column 21, Line 11; Change "(R, and B)" to --(R, G, and B)--.

Column 30, Line 23; Change "fainted" to --formed--.

Column 30, Line 29; Change "phenylfluorene-9-yl)" to --phenylfluoren-9-yl)--.

Column 34, Line 42; Change "5 mL/min After" to --5 mL/min. After--.

Signed and Sealed this
Twenty-sixth Day of April, 2016

Michelle K. Lee
*Director of the United States Patent and Trademark Office*

CERTIFICATE OF CORRECTION (continued)
U.S. Pat. No. 9,196,844 B2

In the Specification:

Column 35, Line 32; Change "2mDBIBPDBq-II)" to --2mDBTBPDBq-II)--.

Column 37, Line 67; Change "15 mL/min After" to --15 mL/min. After--.

In the Claims:

Column 40, Line 63, Claim 6; Change "an alkyl group, or a phenyl group." to --or a phenyl group.--.